US012262950B2

(12) United States Patent
Araci et al.

(10) Patent No.: US 12,262,950 B2
(45) Date of Patent: *Apr. 1, 2025

(54) CLOSED MICROFLUIDIC NETWORK FOR STRAIN SENSING EMBEDDED IN A CONTACT LENS TO MONITOR INTRAOCULAR PRESSURE

(71) Applicant: Smartlens, Inc., Mountain View, CA (US)

(72) Inventors: Ismail Emre Araci, Santa Clara, CA (US); Sevda Agaoglu, Santa Clara, CA (US); Murat Baday, Palo Alto, CA (US); Priscilla Diep, San Jose, CA (US)

(73) Assignee: Smartlens, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/447,033

(22) Filed: Aug. 9, 2023

(65) Prior Publication Data

US 2023/0380686 A1    Nov. 30, 2023

Related U.S. Application Data

(63) Continuation of application No. 17/137,067, filed on Dec. 29, 2020, now Pat. No. 11,759,107, which is a
(Continued)

(51) Int. Cl.
*A61B 3/16* (2006.01)
*G02C 7/04* (2006.01)

(52) U.S. Cl.
CPC ............... *A61B 3/16* (2013.01); *G02C 7/04* (2013.01); *A61B 2562/0261* (2013.01)

(58) Field of Classification Search
CPC .............. A61B 3/16–165; A61B 3/107; A61B 2562/0261–0266; G02C 7/04–049
See application file for complete search history.

(56) References Cited

U.S. PATENT DOCUMENTS 3,228,741 A    1/1966    Becker
5,840,041 A    11/1998   Petter et al.
(Continued)

FOREIGN PATENT DOCUMENTS

CN    103415244 A    11/2013
CN    204394461 U    6/2015
(Continued)

OTHER PUBLICATIONS

Agaouglu et al. Ultra-sensitive microfluidic wearable strain sensor for intraocular pressure monitoring. Lab on a Chip, Issue 22, 2018; pp. 3471-3483.
(Continued)

*Primary Examiner* — Thaddeus B Cox
(74) *Attorney, Agent, or Firm* — Wilson Sonsini Goodrich & Rosati

(57) ABSTRACT

A microfluidic strain sensing device for monitoring intraocular pressure. The device has a contact lens and a closed microfluidic network embedded with the contact lens. The network has a volume that is sensitive to an applied strain. The network distinguishes: (i) a gas reservoir containing a gas, (ii) a liquid reservoir containing a liquid that changes volume when the strain is applied, and (iii) a sensing channel able to hold the liquid within the sensing channel. The sensing channel connects the gas reservoir on one end and connects the liquid reservoir on another end. The sensing channel establishes a liquid-gas equilibrium pressure interface and equilibrium within the sensing channel, which would fluidically change as a response to radius of curvature variations on a cornea, or as a response to mechanical
(Continued)

stretching and release of the cornea. The liquid-gas equilibrium pressure interface and equilibrium are used for measuring the intraocular pressure.

35 Claims, 19 Drawing Sheets

Related U.S. Application Data continuation of application No. 16/124,630, filed on Sep. 7, 2018, now Pat. No. 10,898,074.

(56) References Cited

U.S. PATENT DOCUMENTS

| | | |
|---|---|---|
| 6,645,432 B1 | 11/2003 | Anderson et al. |
| 6,686,184 B1 | 2/2004 | Anderson et al. |
| 7,267,938 B2 | 9/2007 | Anderson et al. |
| 7,531,120 B2 | 5/2009 | Van Rijn et al. |
| 7,670,556 B2 | 3/2010 | Corn et al. |
| 7,835,013 B2 | 11/2010 | Jones et al. |
| 7,887,508 B2 | 2/2011 | Meng et al. |
| 7,927,783 B2 | 4/2011 | Aizenberg et al. |
| 7,981,097 B2 | 7/2011 | Paoli, Jr. |
| 8,088,615 B2 | 1/2012 | Ausserre |
| 8,124,029 B2 | 2/2012 | Polwart et al. |
| 8,220,494 B2 | 7/2012 | Studer et al. |
| 8,263,129 B2 | 9/2012 | DeSIMONE et al. |
| 8,308,686 B2 | 11/2012 | Meng et al. |
| 8,850,895 B2 | 10/2014 | Yan et al. |
| 8,985,763 B1 | 3/2015 | Etzkorn et al. |
| 9,046,641 B2 | 6/2015 | Lai et al. |
| 9,289,123 B2 | 3/2016 | Weibel et al. |
| 9,964,780 B2 | 5/2018 | Pugh et al. |
| 9,977,258 B2 | 5/2018 | Pugh et al. |
| 10,016,132 B2 | 7/2018 | Mandel et al. |
| 10,085,637 B2 | 10/2018 | Araci et al. |
| 10,139,522 B2 | 11/2018 | Marullo et al. |
| 10,219,696 B2 | 3/2019 | Araci et al. |
| 10,898,074 B2 | 1/2021 | Araci et al. |
| 11,213,203 B2 | 1/2022 | Mandel et al. |
| 11,759,107 B2 | 9/2023 | Araci et al. |
| 2002/0052544 A1 | 5/2002 | Jeffries et al. |
| 2004/0169932 A1 | 9/2004 | Esch et al. |
| 2004/0254438 A1 | 12/2004 | Chuck et al. |
| 2006/0055884 A1 | 3/2006 | Molinari et al. |
| 2009/0076367 A1 | 3/2009 | Sit et al. |
| 2010/0016704 A1 | 1/2010 | Naber et al. |
| 2011/0015512 A1 | 1/2011 | Pan et al. |
| 2012/0253165 A1 | 10/2012 | Yen et al. |
| 2013/0041245 A1 | 2/2013 | Cerboni |
| 2013/0055819 A1 | 3/2013 | Yan |
| 2013/0184554 A1 | 7/2013 | Elsheikh et al. |
| 2013/0253451 A1 | 9/2013 | Kim |
| 2013/0278887 A1 | 10/2013 | Legerton |
| 2014/0163351 A1 | 6/2014 | Wang et al. |
| 2014/0197558 A1 | 7/2014 | Linhardt et al. |
| 2014/0243645 A1 | 8/2014 | Leonardi |
| 2014/0343387 A1 | 11/2014 | Pugh et al. |
| 2014/0354942 A1 | 12/2014 | Pugh et al. |
| 2015/0057593 A1 | 2/2015 | Johnson et al. |
| 2015/0148648 A1 | 5/2015 | Pugh |
| 2015/0164321 A1 | 6/2015 | Weibel et al. |
| 2016/0007851 A1 | 1/2016 | Araci et al. |
| 2016/0015265 A1 | 1/2016 | Mandel et al. |
| 2016/0051143 A1 | 2/2016 | Rickard et al. |
| 2016/0262616 A1 | 9/2016 | Araci et al. |
| 2016/0270656 A1 | 9/2016 | Samec et al. |
| 2017/0000341 A1 | 1/2017 | Samec et al. |
| 2017/0165439 A1 | 6/2017 | Kaufmann |
| 2017/0181626 A1 | 6/2017 | Shau et al. |
| 2017/0184875 A1 | 6/2017 | Newman |
| 2017/0280997 A1 | 10/2017 | Lai et al. |
| 2018/0279870 A1 | 10/2018 | Walsh et al. |
| 2018/0296390 A1 | 10/2018 | Hoare |
| 2019/0076021 A1 | 3/2019 | Araci et al. |
| 2020/0138669 A1 | 5/2020 | Berdahl et al. |
| 2021/0113083 A1 | 4/2021 | Araci et al. |
| 2021/0298677 A1 | 9/2021 | Dana et al. |
| 2021/0369111 A1 | 12/2021 | Dana et al. |
| 2022/0022744 A1 | 1/2022 | Dana et al. |
| 2022/0361751 A1 | 11/2022 | Dana et al. |

FOREIGN PATENT DOCUMENTS

| | | |
|---|---|---|
| CN | 105934194 A | 9/2016 |
| CN | 105962887 A | 9/2016 |
| CN | 105962887 B | 9/2017 |
| CN | 107908015 A | 4/2018 |
| EP | 3894167 A1 | 10/2021 |
| JP | H06289333 A | 10/1994 |
| JP | 2013541049 A | 11/2013 |
| JP | 2016527561 A | 9/2016 |
| JP | 2018517929 A | 7/2018 |
| JP | 2018518700 A | 7/2018 |
| WO | WO-9743614 A1 | 11/1997 |
| WO | WO-2014137840 A1 | 9/2014 |
| WO | WO-2016173554 A1 | 11/2016 |
| WO | WO-2017182817 A1 | 10/2017 |
| WO | WO-2018221687 A1 | 12/2018 |
| WO | WO-2019175667 A1 | 9/2019 |
| WO | WO-2020060558 A1 | 3/2020 |
| WO | WO-2020124074 A1 | 6/2020 |
| WO | WO-2020146714 A1 | 7/2020 |
| WO | WO-2020210322 A1 | 10/2020 |
| WO | WO-2021154729 A1 | 8/2021 |
| WO | WO-2022182629 A1 | 9/2022 |

OTHER PUBLICATIONS

Chen et al., Soft wearable contact lens sensor for continuous intraocular pressure monitoring, Medical Engineering & Physics, vol. 36, Issue 9, Sep. 2014, pp. 1134-1139.
EP18934447.6 Extended Search Report dated Mar. 10, 2022.
EP19894568.5 Extended Search Report dated Aug. 8, 2022.
EP20738775.4 Extended Search Report dated Sep. 6, 2022.
International Search Report for PCT/US2020/027221 on Jun. 19, 2020.
International Search Report and Written Opinion for PCT/US2019/066512 on Apr. 14, 2020.
Kim et al., Wearable smart sensor systems integrated on soft contact lenses for wireless ocular diagnostics, Nature Communications, vol. 8 , Apr. 27, 2017 , Article No. 14997.
Notice of allowance dated Oct. 6, 2020 for U.S. Appl. No. 16/124,630.
Office action dated Aug. 11, 2020 for U.S. Appl. No. 16/124,630.
PCT/US2018/052062 International Search Report and Written Opinion of the Searching Authority dated Dec. 11, 2018.
PCT/US2020/013049 International Search Report and Written Opinion of the International Searching Authority dated Mar. 19, 2020.
PCT/US2021/015093 International Search Report & Written Opinion of the International Searching Authority dated Jun. 3, 2021.
PCT/US2022/017224 International Search Report and Written Opinion dated May 11, 2022.
U.S. Appl. No. 13/330,681 Notice of Allowance dated Jul. 7, 2014.
U.S. Appl. No. 13/330,681 Office Action dated Mar. 12, 2014.
U.S. Appl. No. 15/067,378 Notice of Allowance dated Jul. 9, 2018.
U.S. Appl. No. 16/124,630 Corrected Notice of Allowability dated Nov. 23, 2020.
U.S. Appl. No. 17/137,067 Notice of Allowance dated May 19, 2023.
U.S. Appl. No. 17/137,067 Office Action dated Nov. 2, 2022.
Co-pending U.S. Appl. No. 18/500,766, inventors Araci; Ismail Emre et al., filed Nov. 2, 2023.

Patient wears microfluidic contact lens sensor (miLenS)

Image of the IOP sensor

Side view

Top view

Example shapes:

CLOSED MICROFLUIDIC NETWORK FOR STRAIN SENSING EMBEDDED IN A CONTACT LENS TO MONITOR INTRAOCULAR PRESSURE

CROSS-REFERENCE TO RELATED APPLICATIONS

This application is a continuation of U.S. patent application Ser. No. 17/137,067, filed Dec. 29, 2020, now U.S. Pat. No. 11,759,107, which is a continuation of U.S. patent application Ser. No. 16/124,630, filed Sep. 7, 2018, now U.S. Pat. No. 10,898,074, which claims priority from U.S. Provisional Patent Application 62/556,366, filed Sep. 9, 2017, which is incorporated herein by reference.

FIELD OF THE INVENTION

This invention relates to devices, systems and methods to monitor intraocular pressure. In particular, the invention relates to microfluidic network design for strain sensors, which work based on mechanical amplification of the volume of the microfluidic channels, to monitor intraocular pressure.

BACKGROUND OF THE INVENTION

Glaucoma is a neurodegenerative disease that causes irreversible damage to eye's optic nerve, and hence, loss of vision. Continuous and long-term monitoring of intraocular pressure (IOP) is critical for management of glaucoma.

TOP reduction is the only known way of slowing and/or stopping the progression of glaucoma. It is estimated that for every 1 mmHg of TOP reduction, the risk of nerve damage is reduced by 11%. Drug therapy is commonly used to reduce IOP, but there are important challenges that need to be addressed to improve effectiveness of glaucoma treatment. Most importantly, nearly 50% of patients stop er six months for various reasons. Continuous, long-term TOP monitoring that has the capability to measure drug efficacy could help patients stay compliant and help physicians with the management of glaucoma. Moreover, in recent years, diurnal variations in TOP is established as another risk factor for glaucoma, which increased the importance of continuous measurements even further.

Current technologies available for TOP measurements are either not continuous (Goldmann Applanation Tonometry), or continuous but temporary (Sensimed Triggerfish) or continuous but invasive (implantable sensors). The self-tonometry devices (e.g. Icare) can provide long-term data and it is noninvasive but still uncomfortable for the patient to a level that it may require topical anesthetics. Moreover, the results obtained by self-tonometry are found to be user dependent.

Approaches for telemetric continuous TOP measurements have been developed and tested in animal models. Amongst these approaches, contact lens-based monitoring techniques are attractive because they are non-invasive. One contact lens system (Sensimed AG's Triggerfish) measures minute changes in corneal curvature by a contact lens equipped with an electrical strain sensor, an antenna and a microchip that are used for processing and transmitting signal wirelessly. The technology requires the patient to wear a receiver on the waist for data transmission and power transfer. Because of the thick silicone contact lens (central thickness 580 µm), it is not as comfortable as daily used contact lenses; a mild to moderate adverse reactions are reported in up to 80% of patients. The requirement of a trained personnel, and discomfort and high cost associated with this contact lens platform precludes its usage in long term monitoring applications but only allows tests for a single 24-hour period. For this reason, Triggerfish found to be more suitable for determining changes in TOP in a daily scale. However, TOP change as a response to a drug is in the time scale of weeks. Similarly, TOP change in response to certain lifestyle modifications will also be in longer than 24-hour time scale. Therefore, there is a need for a continuous wear contact lens sensor that can monitor TOP variations in long-term for determining the drug efficacy and for decreasing the number of doctor visits that a patient needs to make for routine TOP measurements.

Other examples of contact lens sensors are based on measurement of electrical resistance, inductance and capacitance changes in response to pressure induced strain. In these examples, sensor response is typically detected remotely by measurement of the resonant frequency changes using an external reader coil or by Bluetooth connectivity. The electrical measurements require conductive components inside the lenses, which are typically not transparent and not air. Recently, Kim et al. used graphene-Ag-nanowire to address the electrode transparency issue (J. Kim et al., "Wearable smart sensor systems integrated on soft contact lenses for wireless ocular diagnostics," Nature Communications, vol. 8, April 2017, Art. no. 14997). First condition of a contact lens with long-term usage capability is high air permeability to prevent hypoxia. Unfavorably, the conductive components needed by electrical sensors are impermeable to gases. Metals have 810 orders of magnitude lower gas permeability compared to soft materials and this cause mild adverse reactions in human trials when electrical sensing-based contact lenses are used even for a single 24 hours. The other condition for long term usage is comfort, which is achieved by making high water content and thin (<200 micrometer) contact lenses. The electrical sensing methods are sensitive to the hydration level of the contact lens. Therefore, the contact lens electrical sensors are made of silicone, which have very low water content, instead of the standard silicone/hydrogel materials. This reduces the comfort of the contact lens. There are three main reasons for sensitivity to hydration level. First, swelling of the hydrogel due to hydration induces a strain, and therefore, it is a source of error in measurement. Second, the friction between contact lens and cornea can be sensitive to hydration level, hence influences the sensitivity. Finally, the electrical components are affected from the humidity, and therefore, should be isolated by using sealant materials such as parylene-c.

The present invention advances the art and provides technology to measure TOP eliminating at least some of the current problems or concerns.

SUMMARY OF THE INVENTION

The invention pertains to a strain sensor using microfluidic principles integrated with a contact lens for TOP measurements. The materials used in the invention are low-cost, transparent, air permeable, and flexible. A method is provided to embed the microfluidic strain sensor in a silicone contact lens. The microfluidic contact lens sensor (miLenS) allows patients to measure their own TOP to better manage the glaucoma.

The microfluidic contact lens sensor is capable of measuring the TOP fluctuations due to internal (i.e. metabolism, blinking and saccadic eye movements) as well as external factors (i.e. drugs, diet, lifestyle etc.) during the lifetime of the patient. The measurements will be done at the discretion of the patient (or automatically) where readout will be realized by a smartphone camera (or by a wearable camera for automated measurements). This allows for at-home monitoring and continuous data recording. The data then will be sent directly to a medical provider's database, which allows patients and physicians to monitor TOP variations. Aspects of our technology are listed as follows:

a. The miLenS will be built using a hybrid material system where the narrow microfluidic sensing region (as low as 0.1 mm wide ring at the periphery of miLenS) is embedded in a silicone or silicone/hydrogel contact lens material. The microfluidic sensing channels will be made out of transparent, soft, and oleophobic materials. The sensing material will be 6-10 orders of magnitude more air permeable compared to electronic components.

b. The microfluidic sensing technique has no actively controlled components and only works based on the principles of fluid physics. The miLenS is free of all electrical components (powerless). It is a low-cost device. Additionally, this provides easier usability by eliminating the cumbersome peripheral components (e.g. antenna, microchip etc.) for data transmission, reception and recording, which are needed in wearable electronic sensors.

c. The sensor will be sensitive to strain and responds to corneal radius of curvature changes but has low sensitivity to forces applied directly by the eyelid or due to hydration of the contact lens materials. The sensor we designed has low stiffness in lateral direction (i.e. the microfluidic device is thin and has low elastic modulus) and high stiffness in radial direction (i.e. the microfluidic network channels have small width), which will make it insensitive to external forces (e.g. blinking, rubbing of the eye).

d. The miLenS enables readout with a smartphone camera and an optical adaptor. This will provide measurements at discrete time points. In one variation, a wearable camera that can track the sensor response can also be utilized for continuous and automated measurements.

e. Continuous data recorded with existing technologies show that TOP fluctuates around 5-15 mmHg day-to-day and hour-to-hour, and 15-40 mmHg second-to-second. The microfluidic network circuitry we have designed has the capability to filter out large fluctuations that occurs in short time scales due to blood pressure or muscle contractions. In this case, the sensor actually acts as a fluidic low-pass filter, which only responds to changes that occur in minutes or slower. In a similar manner, the fluidic components can be designed to register only the rapid TOP changes. A sensor that can measure events happening in different time scales can make better estimation of the true TOP based on the corneal radius of curvature measurements.

The microfluidic strain sensor embedded contact lens is convenient to use and has continuous measurement capability. It requires minimal training to take measurements therefore, will be used as a device for home-medicine. These will enable clinical studies where recording of long-term TOP data on large patient populations is needed. Continuous recording of TOP and its analysis will improve our understanding of neurodegenerative diseases and their relation to pressure.

Additionally, it will be useful for improving the efficiency and efficacy of drugs that are used for glaucoma treatment. Therefore, miLenS technology offers a promising healthcare technology for better personalized care of glaucoma patients. These advantages listed above will potentially enable the patient to use the sensor permanently and without the trained personnel assistance.

In one embodiment, the present invention provides a microfluidic strain sensing device for monitoring intraocular pressure changes. The closed microfluidic network is transparent and/or oleophobic. The microfluidic strain sensing device has a contact lens and a dosed microfluidic network embedded with the contact lens. The contact lens is a silicone contact lens, a hydrogel contact lens or a combination thereof. The contact lens has no actively controlled components or electrical components.

The closed microfluidic network has a volume that is sensitive to an axial strain. The closed microfluidic network distinguishes: (i) a gas reservoir containing a gas, (ii) a liquid reservoir containing a liquid that changes volume when the strain is induced, and (iii) a sensing channel able to hold the liquid within the sensing channel. The sensing channel connects the gas reservoir on one end and connects the liquid reservoir on another end. The sensing channel establishes a liquid-gas equilibrium pressure interface and equilibrium within the sensing channel, which would fluidically change as a response to radius of curvature variations on a cornea, or as a response to mechanical stretching and release of the cornea. The liquid-gas equilibrium pressure interface and equilibrium are used for measuring the intraocular pressure.

The liquid reservoir forms at least one ring and wherein the air reservoir is positioned inside or outside the at least one ring. In each case, the liquid reservoir volume is highly sensitive to tangential forces on the eye relative to radial forces on an eye wearing the contact lens. The liquid reservoir has a high stiffness in radial direction and/or smaller channel width relative to the stiffness in tangential direction and/or a microfluidic channel wall thickness resulting in the liquid reservoir becoming insensitive to external forces.

In one example, the liquid reservoir has one or more chambers. These chambers could have concentric rings. These chambers could also have concentric rings that are connected to each other at one or more locations. These chambers could also have concentric rings where the sensitivity increases as the number of concentric rings increases.

In one example, the surface of the liquid reservoir could be patterned. The surface of the liquid reservoir ceiling could have a convex shape and the convex shape could be curved towards the reservoir channel floor.

The sensing channel has a strain sensitivity of about 4.5 mm interface movement per about 1% strain applied to the liquid reservoir. In one example, the sensing channel has an inner diameter of about 1-10 mm. In another example, the sensing channel has an inner diameter 5-12 mm with a cross sectional area of $10^{-11}$-$10^{-8}$ m$^2$.

BRIEF DESCRIPTION OF THE DRAWINGS

FIG. 4 illustrates this: basically, the microfluidic channel ceiling thickness t1 and floor thickness t2 has to be small (<20 µm). This also reduces the stiffness in both directions. The reservoir ring width w has to be small (<100 µm). This does not affect the tangential stiffness but increases the radial stiffness of the microfluidic channel and is key in increasing the sensor performance.

FIG. 5 shows according to an exemplary embodiment of the invention top views of a single ring liquid reservoir versus a three rings reservoir. The circled region for the three rings shows the rings zoomed in.

DETAILED DESCRIPTION

IOP measurement devices reported so far do not consider the directionality of the forces acting on the sensors. For example, capacitance measurement-based sensor by Chen et al. (G.-Z. Chen, I.-S. Chan, L. K. K. Leung, and D. C. C. Lam, "Soft wearable contact lens sensor for continuous intraocular pressure monitoring," *Medical Engineering & Physics, vol.* 36, no. 9, pp. 1134-1139, September 2014), responds to the radial forces applied on the lens such as due to blinking. An ideal contact lens sensor should only be sensitive to the strain applied in result of the radius change of the cornea, but should not be affected by the forces applied perpendicularly on the lens (i.e. radial forces). In consideration of this, we have used COMSOL simulations and experimental measurements to develop a strain sensor, which is more sensitive to tangential forces than the radial forces on the eye. Embodiments of the invention are based on microfluidic sensing for IOP measurements and such desired strain sensor force response.

Figure 1:
FIG. 1 shows according to an exemplary embodiment of the invention a workflow of the miLens device based on pressure monitoring.
Figure 1:
Figure 1:
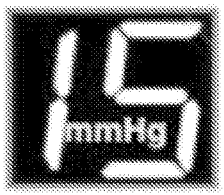
Figure 1:
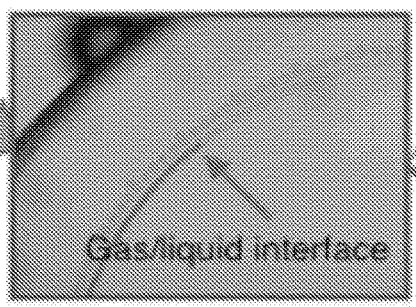

FIG. 1 shows an example of a workflow of the IOP self-measurement technique. The miLenS is distinct from other sensors because patients will be able to place and remove it by themselves similar to a regular contact lens. As IOP fluctuates, radius of corneal curvature changes (each 1 mmHg change in IOP causes 4 µm change in radius of curvature). In this technology, the fluidic level in the microfluidic sensing channel of the sensor will change as a response to radius of curvature variations on the cornea. The sensor response will be detected with a smartphone camera equipped with an optical adaptor and then converted to pressure value by a smartphone app. It will eliminate the security and health concerns related to radio frequency or Bluetooth data transfer methods. We have demonstrated an IOP detection limit of 1 mmHg on enucleated porcine eyes, which is sufficient for IOP monitoring applications.

Microfluidic circuits, analogous to electronic circuits, can function as low or high pass filters (electrical resistance and capacitance are replaced by fluidic resistance (R) and the compliance (C) of compressible materials, respectively). The RC value will determine the time constant of the sensor response. Sensors with large RC values will not respond to fast changes but will be sensitive to slowly varying diurnal variations. Sensors with small RC values will have the capability to detect the effects of blinking and ocular pulsation.

Figure 2A:
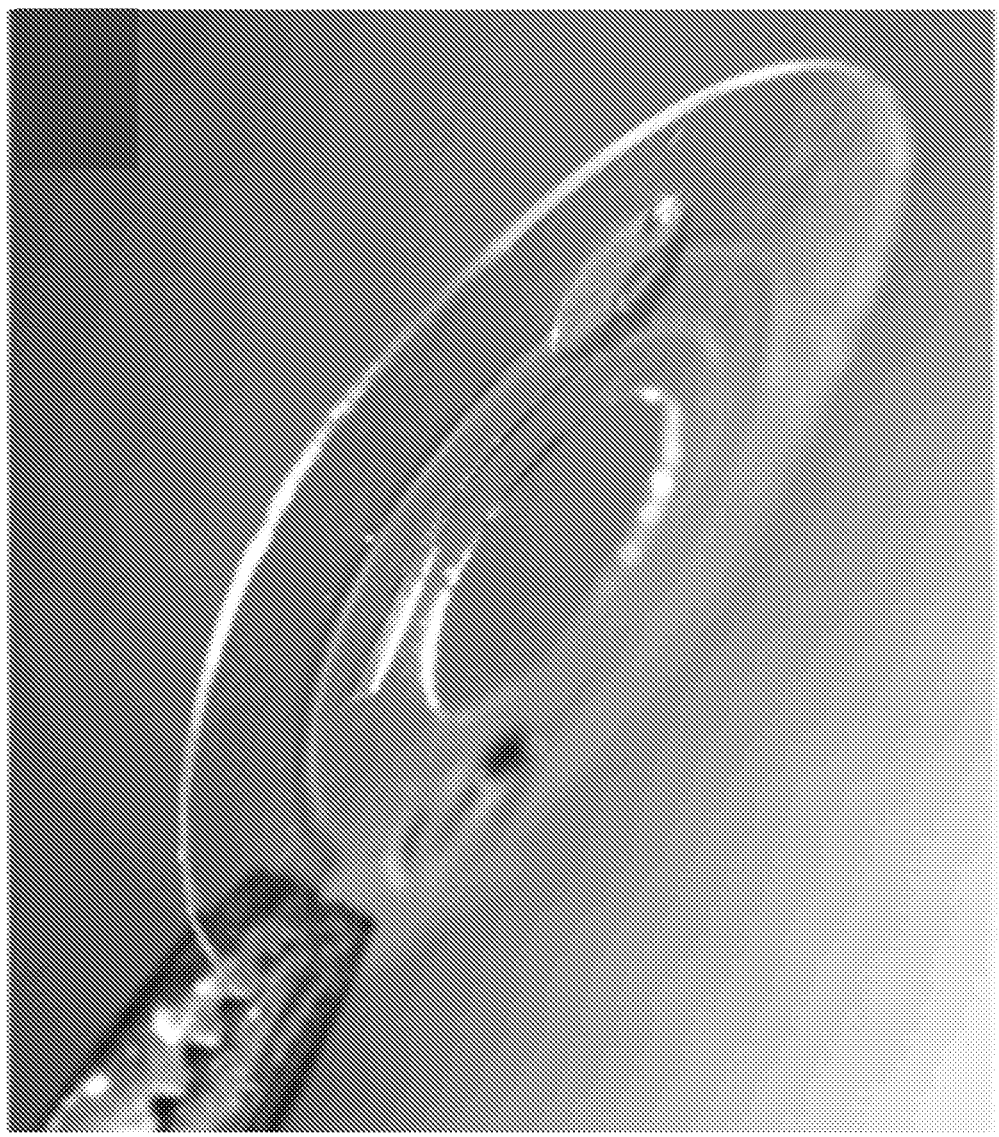
FIG. 2A shows according to an exemplary embodiment of the invention an image of a sensor which is only 100 micrometers thick. The small drops on each side are Norland Optical Adhesive (NOA) used to seal the sensor and can be made less than 20 micrometers thick.
Figure 2B:
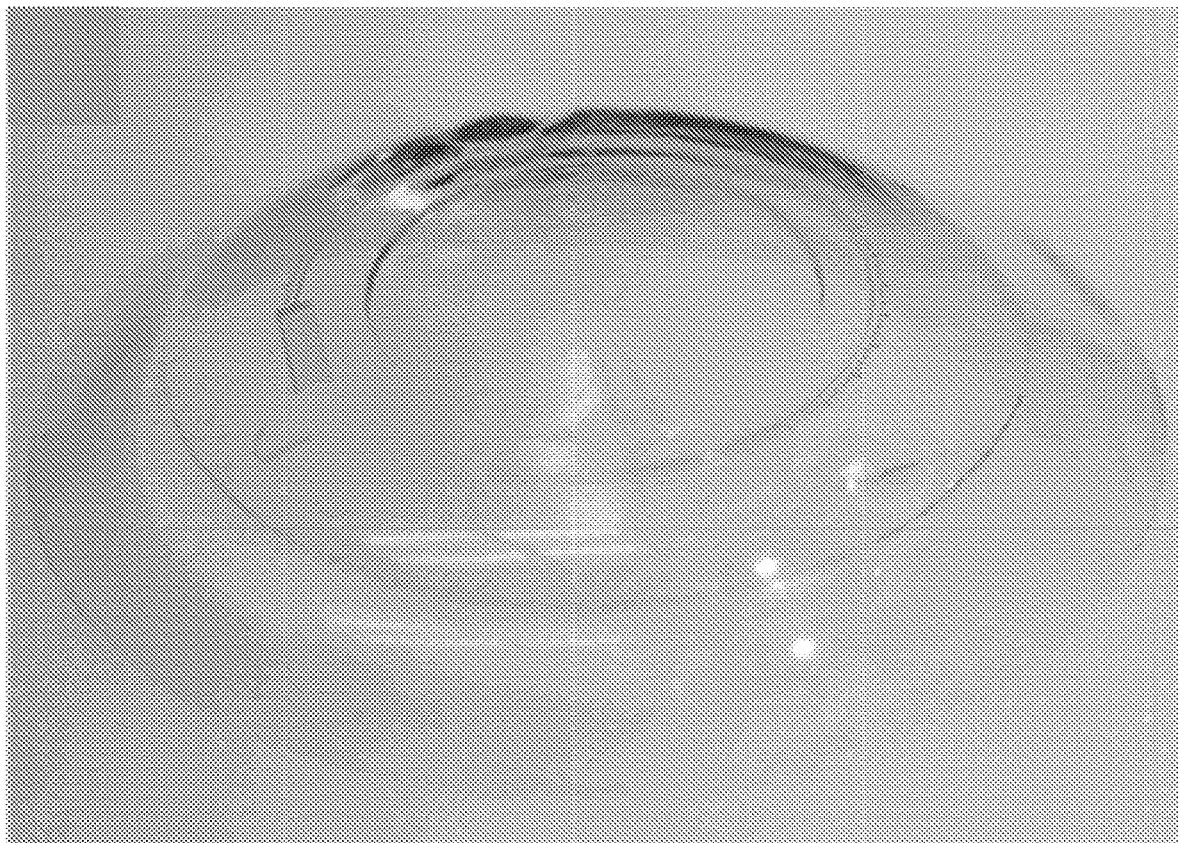
FIG. 2B shows according to an exemplary embodiment of the invention an image of a sensor after embedding the sensor into the contact lens (300 micrometers final thickness).
Figure 3:
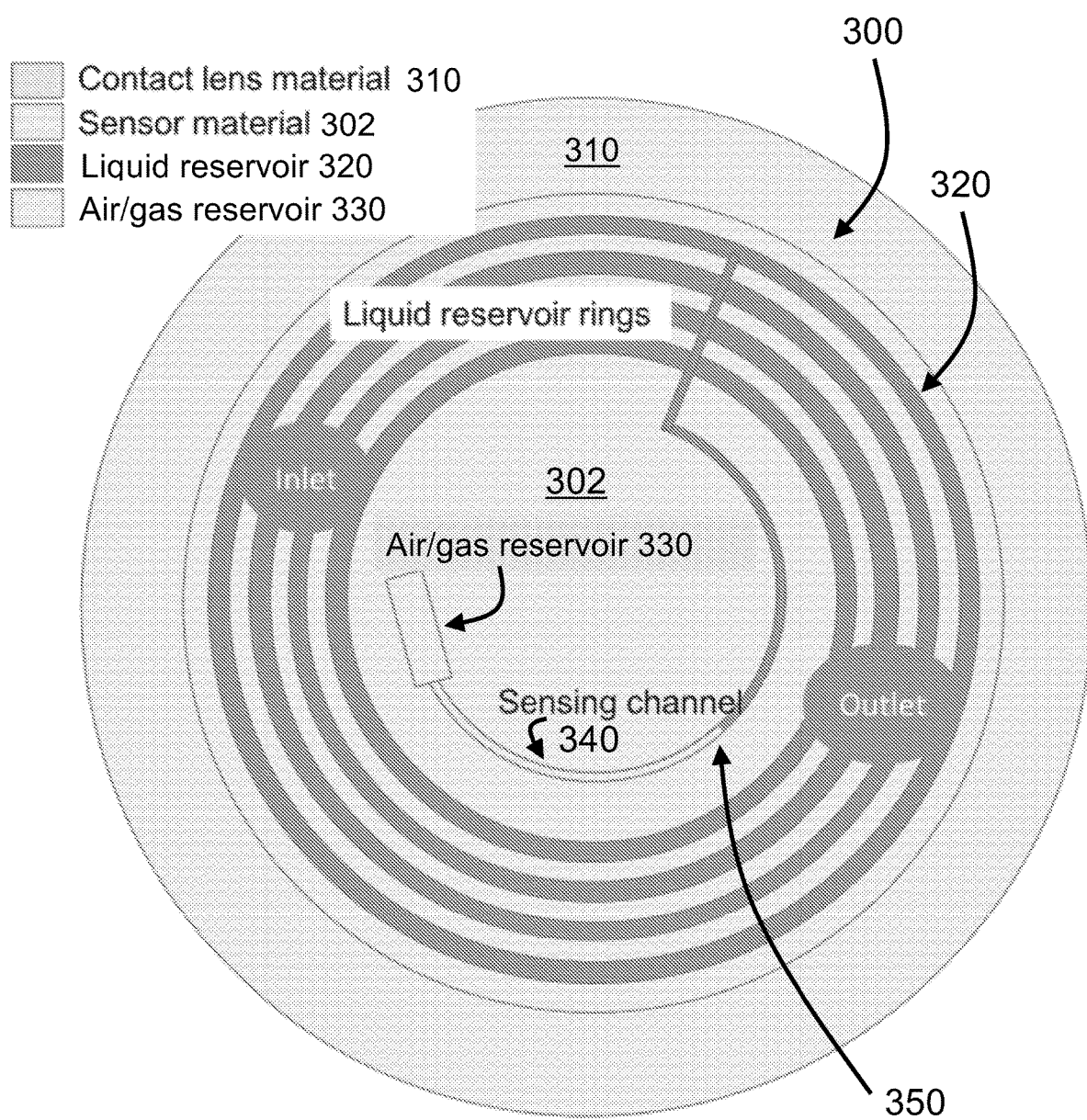
FIG. 3 shows according to an exemplary embodiment of the invention a top view of a closed system sensor with multiple ring liquid reservoir embedded in a contact lens.
Figure 4:
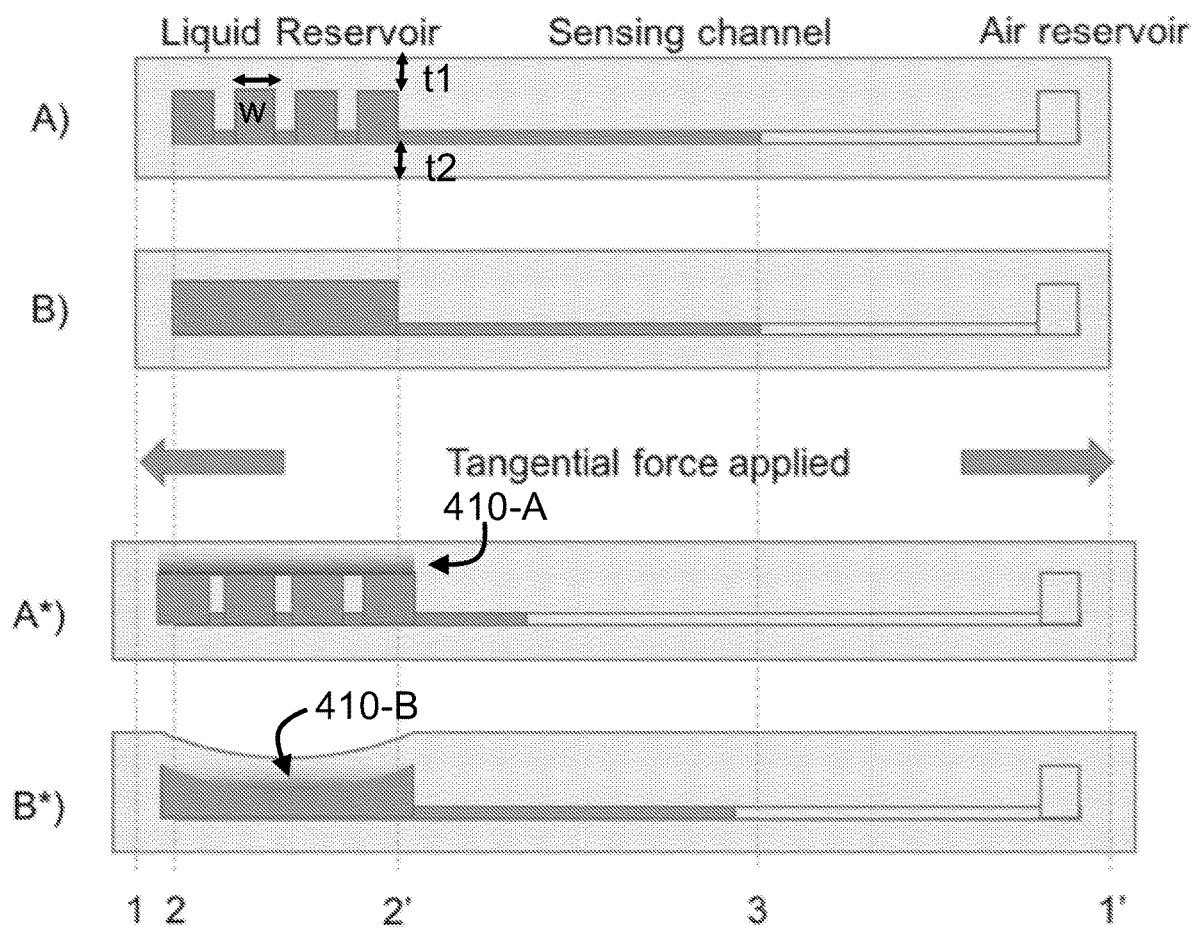
FIG. 4 shows according to an exemplary embodiment of the invention a side view of a multiple chamber liquid reservoir sensor A) versus a single chamber liquid reservoir sensor B) and their respective behavior when the sensors are stretched under tangential forces as shown in A*) and B*). 410-A and 410-B show possible stretch points under stretching of the sensor. The sensor has to be made from a soft material decreasing the stiffness in both directions. The sensor has to be thin.

In one exemplary embodiment, the microfluidic strain sensor (FIG. 2A) is integrated into a PDMS contact lens (FIG. 2B) for wearable sensing applications. Referring to FIGS. 3-4, sensor 300 with sensor material 302, the sensor 300 is embedded in contact lens 310 distinguishes a liquid reservoir 320 (amplifies the displaced liquid volume and show in this example as liquid reservoir rings), a gas reservoir 330 and a sensing channel 340 connected to the liquid reservoir 320 on one end and to a gas reservoir 330 on the other. First, liquid reservoir 320 is filled with a working liquid such as oil using capillary action and then sealed. This creates a stable gas/liquid interface 350 in the sensing channel 340 and forms a closed microfluidic network. The IOP fluctuations change the corneal radius of curvature; for every 1 mmHg increase in IOP, corneal radius of curvature increases 4 µm. This increases the liquid reservoir volume due to the strain applied on the liquid reservoir elastic walls. The increased reservoir volume creates a vacuum and shifts the gas/liquid position 350 in the sensing channel 340 towards the liquid reservoir 320. As the sensing channel cross section area is reduced, the linear liquid displacement required to accommodate the reservoir volume change increases, hence the sensitivity improves.

Figure 5:
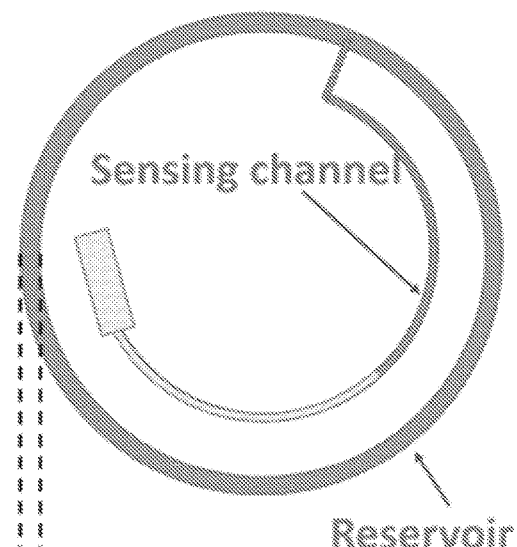
Figure 5:
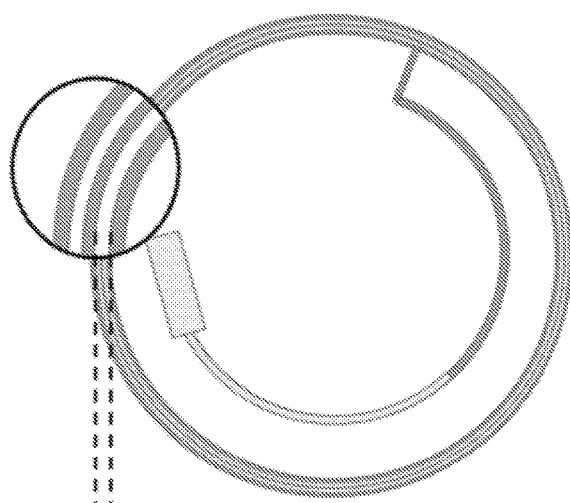
Figure 6:
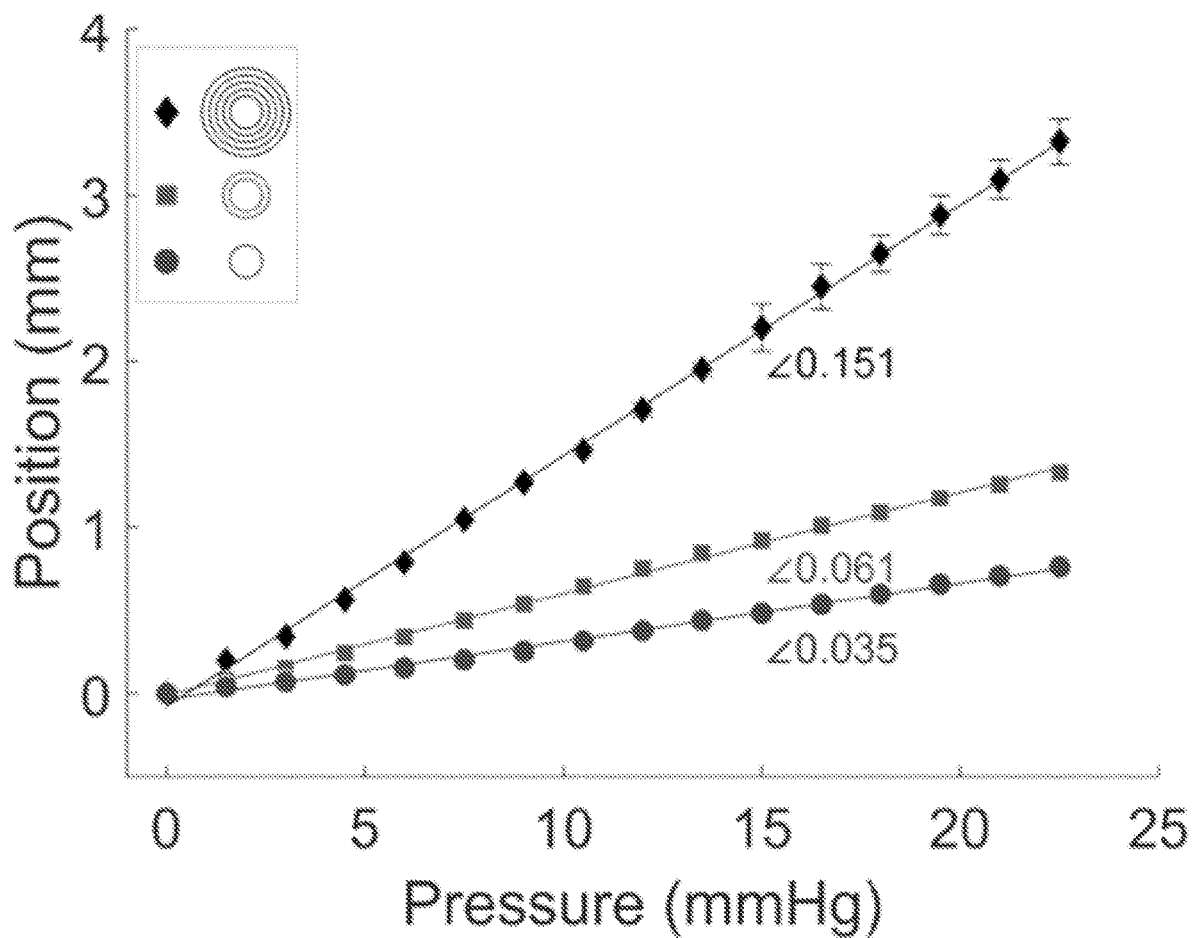
FIG. 6 shows according to an exemplary embodiment of the invention pressure response of three different sensor types; 1, 2, and 5 reservoir rings. Ring height, width and separation is 100 micrometers. The slope values are the sensitivity and shown under corresponding curve in mm per mmHg unit. For each curve, the average and standard deviation of at least 3 measurements are used.
Figure 7:
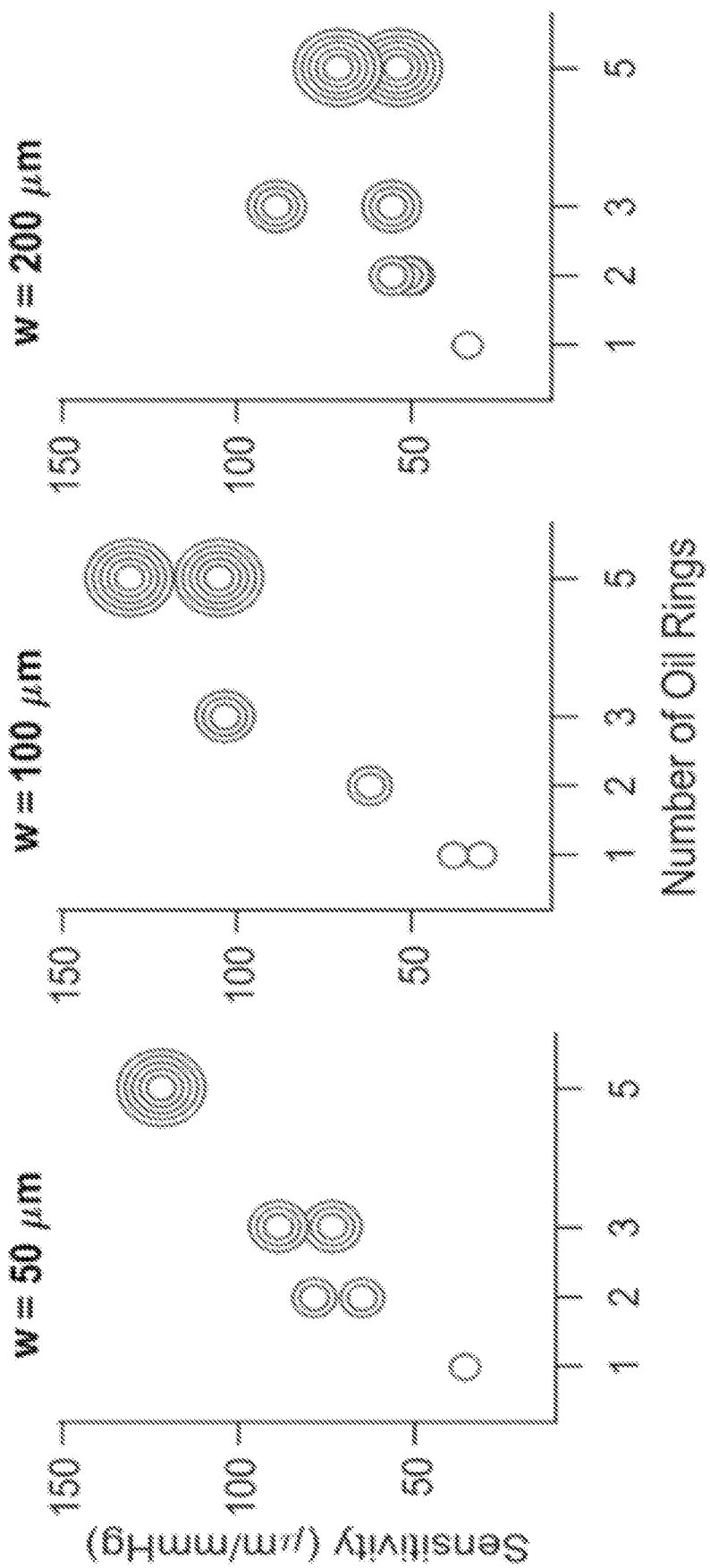
FIG. 7 shows according to an exemplary embodiment of the invention a sensitivity dependence on the number of reservoir rings for three different ring widths. The multiple data points for some of the ring numbers are obtained using sensors fabricated at different times with the same parameters; fluctuations in sensitivity values are in result of fabrication variances. The sensitivity depends linearly on the number of rings with 50 and 100 micrometer widths, but no significantly affected from it for 200 micrometer width.
Figure 8:
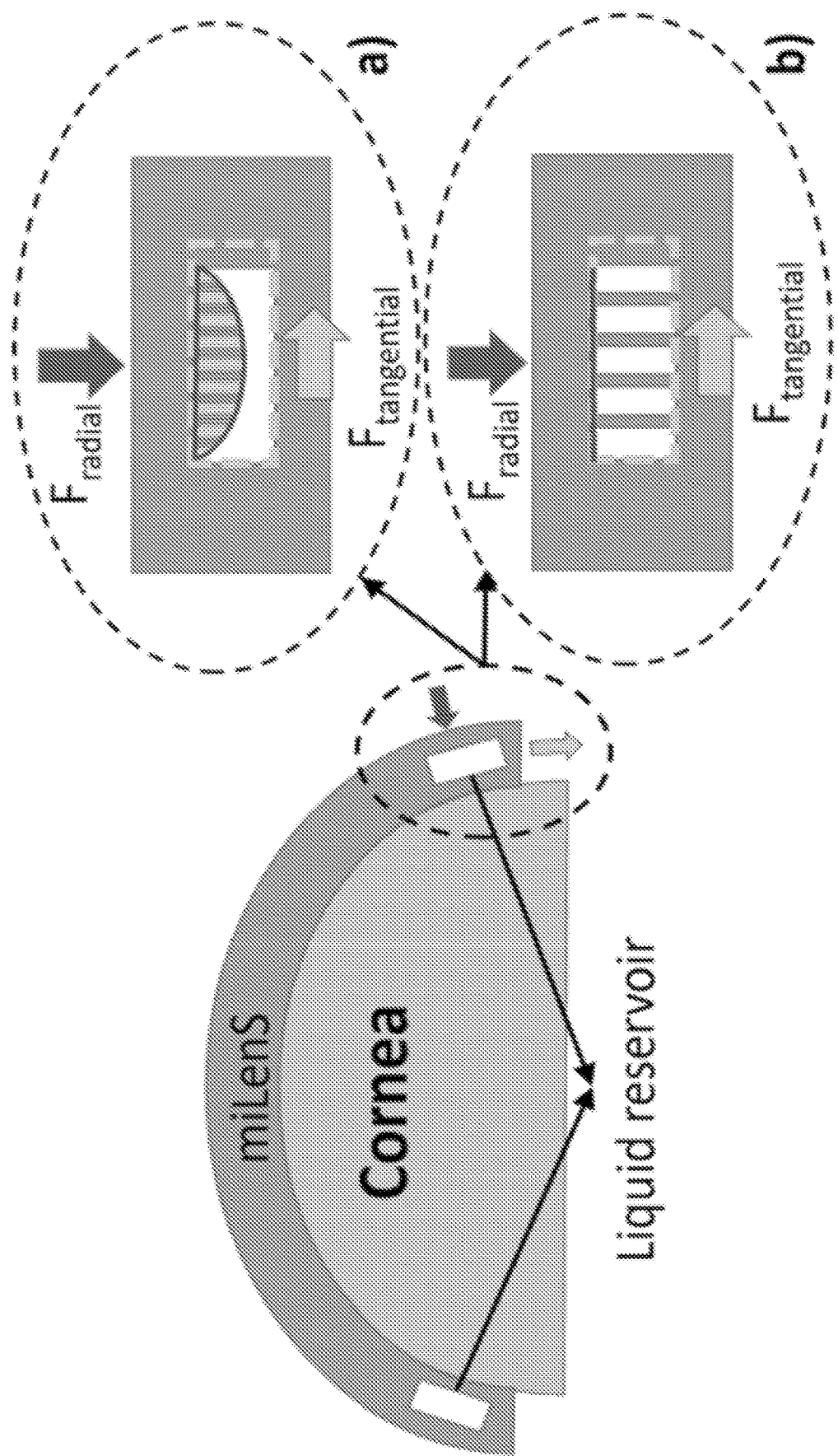
FIG. 8 shows according to an exemplary embodiment of the invention a side view of the placement of the miLenS on a cornea and position of the liquid reservoirs. The insets show the close-up look of the liquid reservoirs and the forces acting on them; inset a) shows a single wide liquid reservoir compressed under radial force, and inset b) shows a series of concentric circles as liquid reservoir not compressed under the same force. As this figure is shown in grey scale, for colors to reflect the effect of the forces, please refer to U.S. Provisional Patent Application 62/556,366 filed Sep. 9, 2017, which is incorporated herein by reference.
Figure 9:
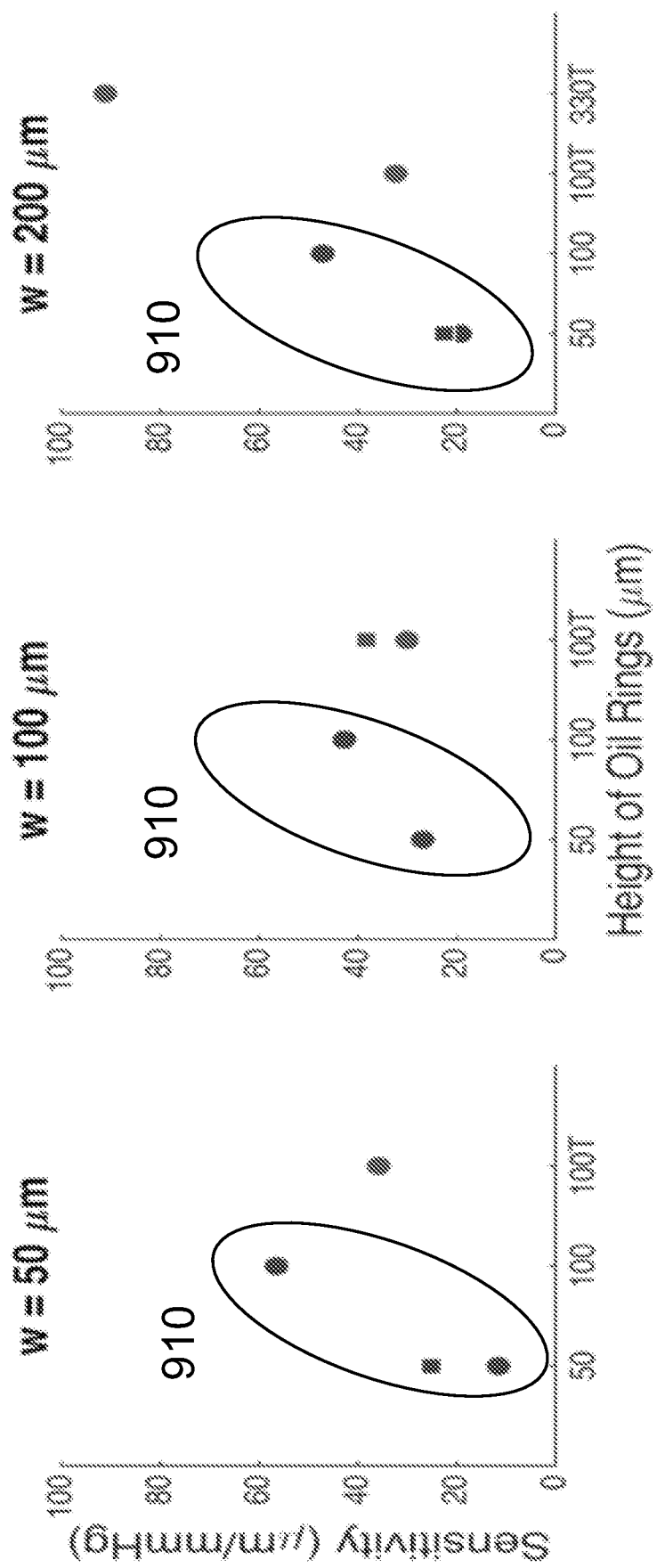
FIG. 9 shows according to an exemplary embodiment of the invention sensitivity dependence on the height for three different ring widths. The multiple data points for some of the heights are obtained using sensors fabricated at different times with same parameters; fluctuations in sensitivity values are the result of fabrication variances. The sensitivity depends linearly on the reservoir height. The red data points 910 indicate thicker chips (300 micrometers) and they show 50% reduced sensitivity compared to thinner (150 micrometers) counterparts 920. As this figure is shown in grey scale, for colors, please refer to U.S. Provisional Patent Application 62/556,366 filed Sep. 9, 2017, which is incorporated herein by reference.

FIG. 5 shows the top view of two example designs—single ring 510 versus three rings 520 for the liquid reservoir—of the microfluidic strain sensor. Increasing the vertical wall surface area of the liquid reservoir increase the sensitivity of the sensor to changes in IOP. This was tested in two ways; i) increasing the number of walls ii) increasing the height of the channel walls. First, we designed and fabricated sensors with multiple liquid reservoir rings as shown by for example 520, thus increasing the total wall surface area. The sensitivity results for different number of rings are presented in FIGS. 6-7. We found that increasing the number of walls by adding more rings, increased the sensitivity of the device in a linear manner. On the contrary, the width of the reservoir did not have a significant effect on the sensitivity. This phenomenon is a direct result of the interplay between tangential strain and radial force induced collapses as shown in FIG. 8. To test the effect of the reservoir wall height we built three types of sensors (50, 100 and 330 µm height) and compared their sensitivity. As shown in FIG. 9, as the reservoir height doubled, the sensitivity is also doubled. When we increased the reservoir height to 330 µm the sensitivity also increased by a factor of three (shown only for 200 µm width), proving the effect of vertical wall height. FIG. 9 further shows the effect of sensor stiffness. When a 150 µm thick sensor is compared to a 300 µm thick one (shown by 100T and 330T), the thicker sensors have −50% lower sensitivity.

In summary, we experimentally scanned a large parameter range to understand and optimize the sensor performance. We have fabricated sensors with varying number of reservoir rings (1-5), ring widths (w=50-500 µm), reservoir heights (50, 100, 330 µm) and chip thicknesses (130 µm, 300 µm) as well as different Young's moduli −1 MPa (PDMS) vs −10 MPa (NOA 65) and −100 MPa (NOA 61). The results of these sensitivity tests have demonstrated that; i) The increased liquid reservoir height increases the sensitivity. ii) We are able to improve the sensitivity by adding more reservoir rings to the design as needed (e.g. depending on the required continuous wear contact lens properties). iii) The stiffness (Young's modulus (E)×chip thickness (t)/width (w)) does not alter the sensitivity significantly; however, it needs to be optimized in view of other factors such as comfort and lens/cornea mechanic interactions.

Auxetic Metamaterials for Microfluidic Strain Sensing

Figure 10:
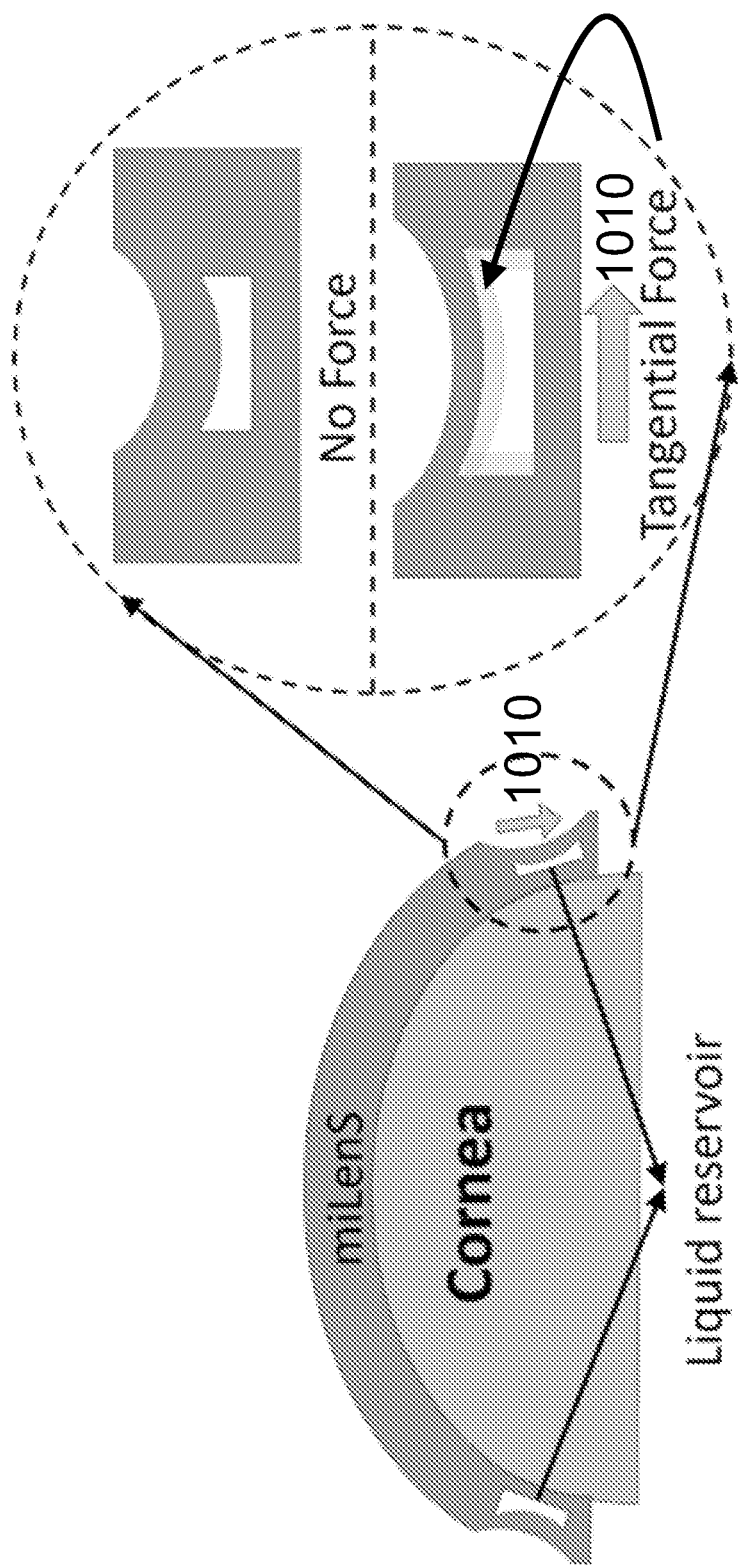
FIG. 10 shows according to an exemplary embodiment of the invention an auxetic contact lens sensor and close-up view of the liquid reservoir cross section. Unlike a sensor with a rectangular channel as shown in FIG. 8, this channel has a curved top layer. This top layer gets flattened when tangential force is applied as shown according to our data and Comsol simulations. As this figure is shown in grey scale, for colors, please refer to U.S. Provisional Patent Application 62/556,366 filed Sep. 9, 2017, which is incorporated herein by reference.
Figure 11:
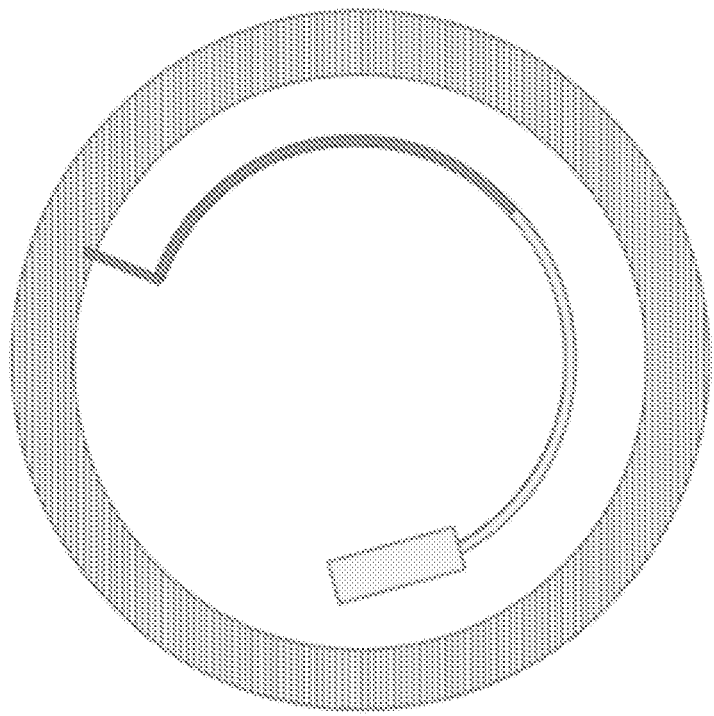
FIG. 11 shows according to an exemplary embodiment of the invention a sensor with a reservoir ceiling patterned with circular and linear convex shapes.
Figure 11:
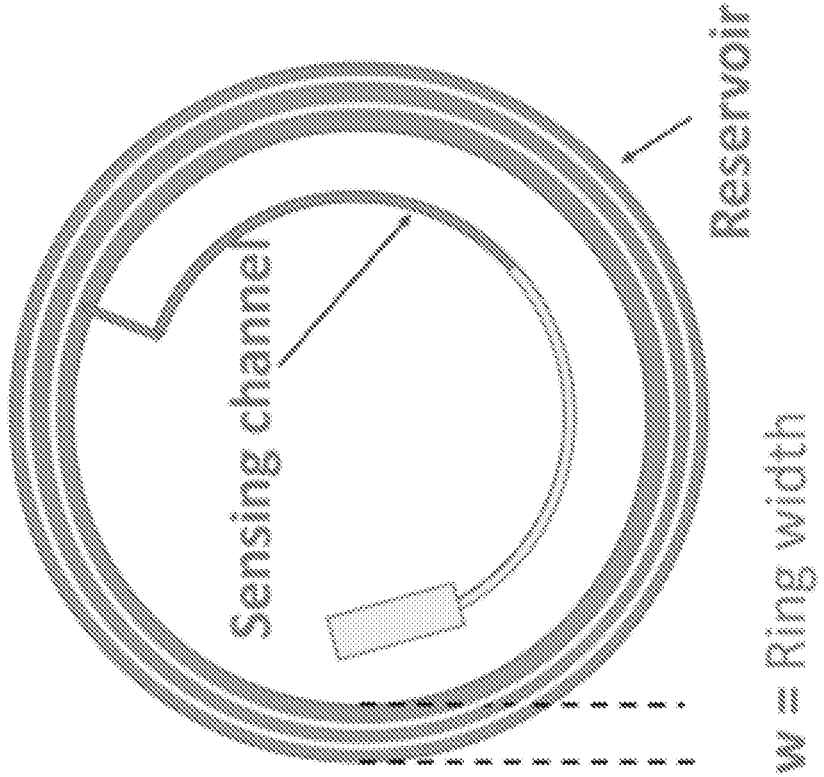

In another version of the sensor, the microfluidic channel network height increases in response to the applied tangential strain 1010. The volume increase is achieved by Poisson ratio modification through lithographical patterning of elastomeric sensor. FIG. 10 shows, via a cross-section of the contact lens sensor, the working principle of the auxetic metamaterials for strain sensing. The ceiling of the microfluidic channel has a convex shape, i.e. curved towards the channel interior, as shown. This is achieved by patterning the ceiling film with either circular or linear patterns as shown in FIG. 11. Although these are the only patterns we tested other patterns can be used to get the same effect. When the tangential force is applied (i.e. due to IOP changes), as shown in FIG. 10, the ceiling gets deformed outward because of the convex ceiling, as opposed to the collapses observed when flat ceiling is used. This deformation towards the front face of the sensor causes a channel height increase, hence amplification in liquid reservoir volume expansion, according to our COMSOL simulations as shown in U.S. Provisional Patent Application 62/556,366 filed Sep. 9, 2017 (FIG. 14 therein), which is incorporated herein by reference. This amplification increases the sensitivity of the sensor.

Figure 12:
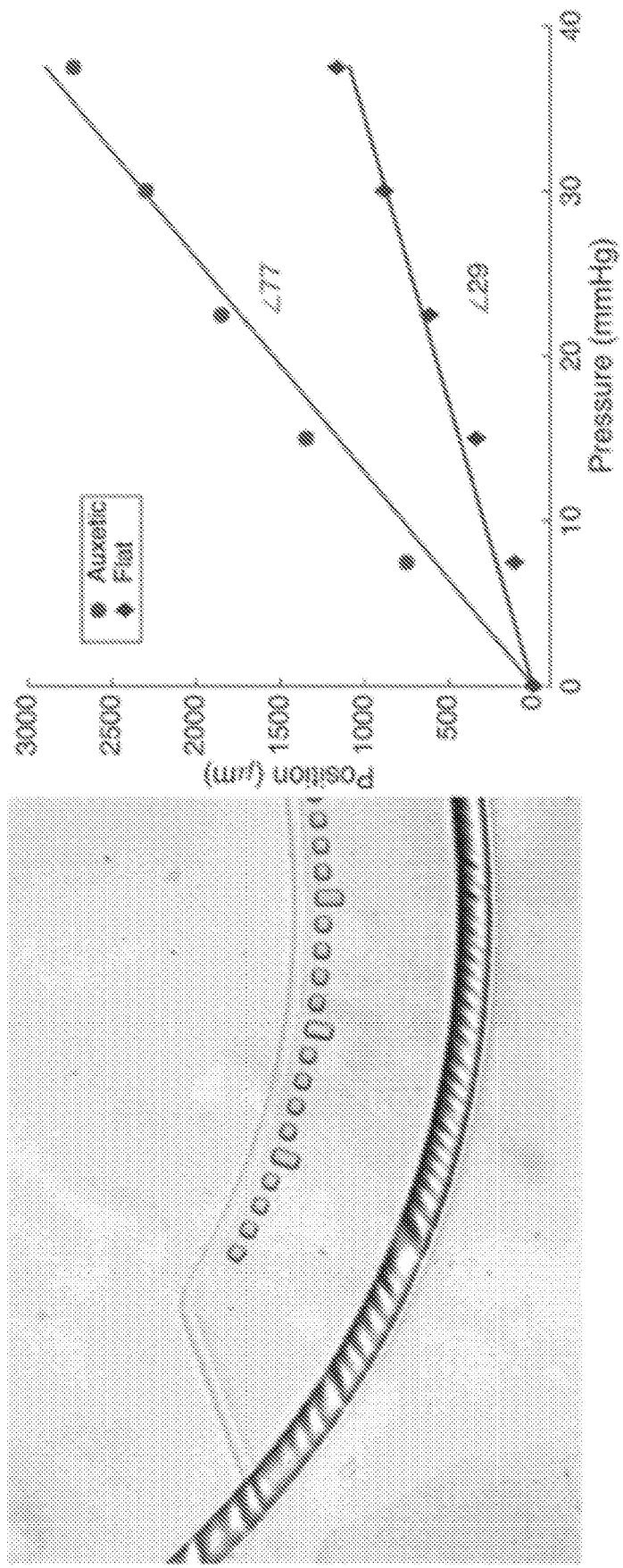
FIG. 12 shows according to an exemplary embodiment of the invention a microscope image of the sensor to the left with a linearly patterned liquid reservoir ceiling. To the right is shown a comparison of measured sensitivity for a flat ceiling sensor verses a curved ceiling.

FIG. 12 on the left shows the image of the liquid reservoir on an auxetic sensor with a linear pattern of convex structures on the ceiling. FIG. 12 on the right shows the experimental sensitivity comparison between flat and curved (auxetic) devices. The sensitivity increase is 2.5-fold.

Microfluidic mechanical metamaterials that are biocompatible and electronics-free enabled fabrication of highly sensitive and reliable strain sensors. The tangential strain-sensing method we developed is specific to TOP as demonstrated by our experiments. We have used this approach to monitor TOP in porcine eyes and demonstrated 1-mmHg detection limit (corresponds to 0.05% strain) and reliability for several weeks. The microfluidic strain sensor can measure the strain of the eye due to the shape changes in response to TOP in the clinically relevant range.

Manufacturing

Figure 13:
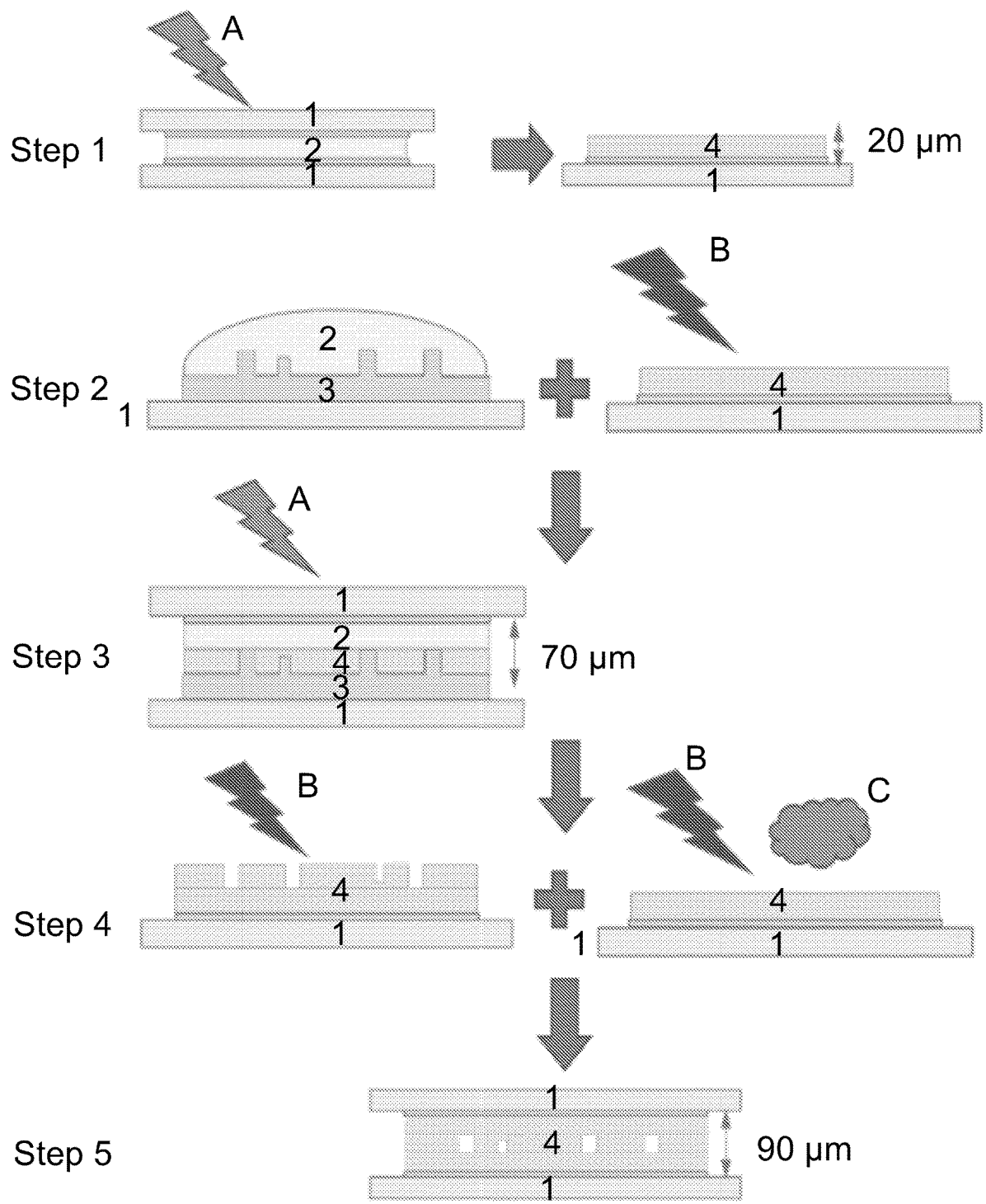
FIG. 13 (auxetic) device 29 micrometer/mmHg and 77 micrometer/mmHg, respectively, shows according to an exemplary embodiment of the invention a method of fabricating the sensor. A refers to UV treatment. B refers to plasma treatment (PDMS). C refers to treatment APTES. 1 refers to glass slide, 2 refers to NOA65 (uncured), 3 refers to PDMS, 4 refers to NOA65 (cured). Step 1 is NOA65 sandwiched in between two PDMS coated glass slides and UV cured to create 20 micrometer films. This is repeated twice. Step 2 is NOA65 dropped on the mold and 20 micrometer films from step 2 is plasma treated. Step 3 is two layers from step 2 are sandwiched together and UV cured. Step 4 is a 70 micrometers layer from step 3 is plasma treated. The 20 micrometers layer from step 1 is plasma treated and APTES treated. Step 5 is two layers from step 4 are sandwiched together. As this figure is shown in grey scale, for colors, please refer to U.S. Provisional Patent Application 62/556,366 filed Sep. 9, 2017, which is incorporated herein by reference.

We built the sensors using photolithography and soft lithography techniques. First, polydimethylsiloxane (PDMS) soft molds were fabricated. As a sensor material, polyurethane based Norland Optical Adhesive 65 (NOA65) was chosen due to its transparency, flexibility, oleophobicity and biocompatibility. Then, thin NOA65 films with the required features were made and bonded together to make sensors as shown in FIG. 13. For the purposes of this invention, we developed specific fabrication methods to build extremely thin (~100 μm) microfluidic devices. The gas permeability of polyurethane used in our devices is 6-8 orders of magnitude lower than metals used in wearable electronics.

Figure 14:
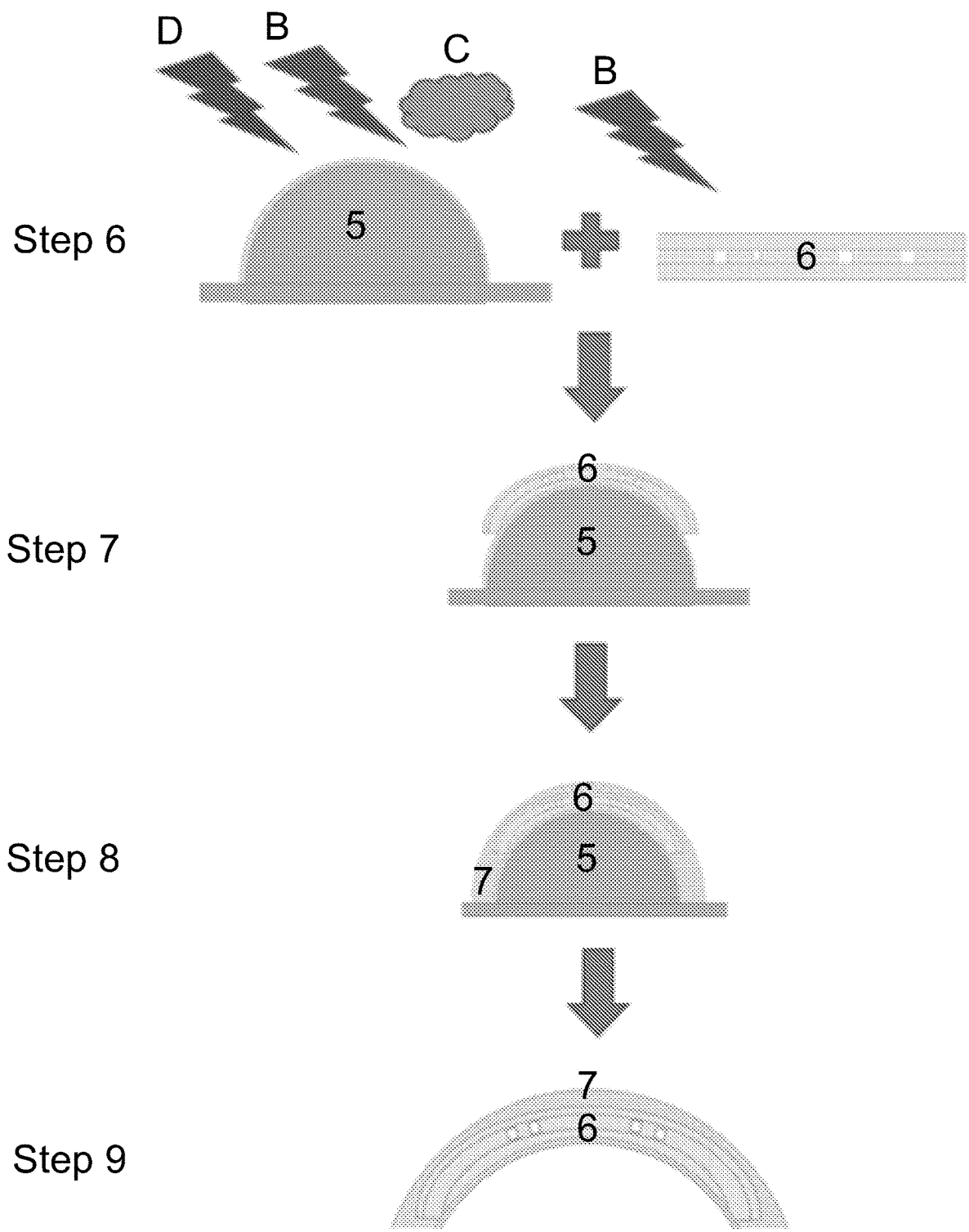
FIG. 14 shows according to an exemplary embodiment of the invention a method of embedding the sensor into a contact lens. B refers to plasma treatment (PDMS). C refers to treatment APTES. D refers to cure (heat) treatment. 5 refers to the hemispherical mold for contact lens fabrication, 6 refers to the sensor, 7 refers to the top layer of the contact lens. Step 6 is PDMS poured on a contact lens mold. Then cured at 80 degrees Celsius, plasma and APTES treated. Sensor bottom surface is plasma treated. Step 7 is sensor bottom surface placed on the PDMS coated contact lens mold. The sensor reservoirs are filled with working liquid and sealed. Step 8 is more PDMS poured on the sensor and cured at room temperature. Step 9 is contact lens peeled off the surface of the mold. As this figure is shown in grey scale, for colors, please refer to U.S. Provisional Patent Application 62/556,366 filed Sep. 9, 2017, which is incorporated herein by reference.

We have first cut the strain sensor into desired shape and embedded a flat 100 μm strain sensor (FIG. 2A) into a PDMS contact lens. Although we have built our sensors flat they can also be built curved if curved molds were used. We have developed a fabrication protocol where we can build contact lenses with 8-15 mm radius of curvature and 10-14 mm radius as shown in FIG. 2B. We have used dome shaped plastic molds where we poured PDMS on them to obtain the 10-100 μm silicone film at the desired radius of curvature, we bonded our sensor on the silicone film by (3-Aminopropyl) triethoxysilane (APTES) chemistry. Then, poured more silicone to fully embed the sensor in silicone. The details are shown in FIG. 14. Finally, we cut out the lenses with circular punchers after curing the silicone at room temperature overnight. We have developed processes and techniques to build sensors as low as 50 μm thick so that overall contact lens sensor can be less than 150 μm.

Figure 15:
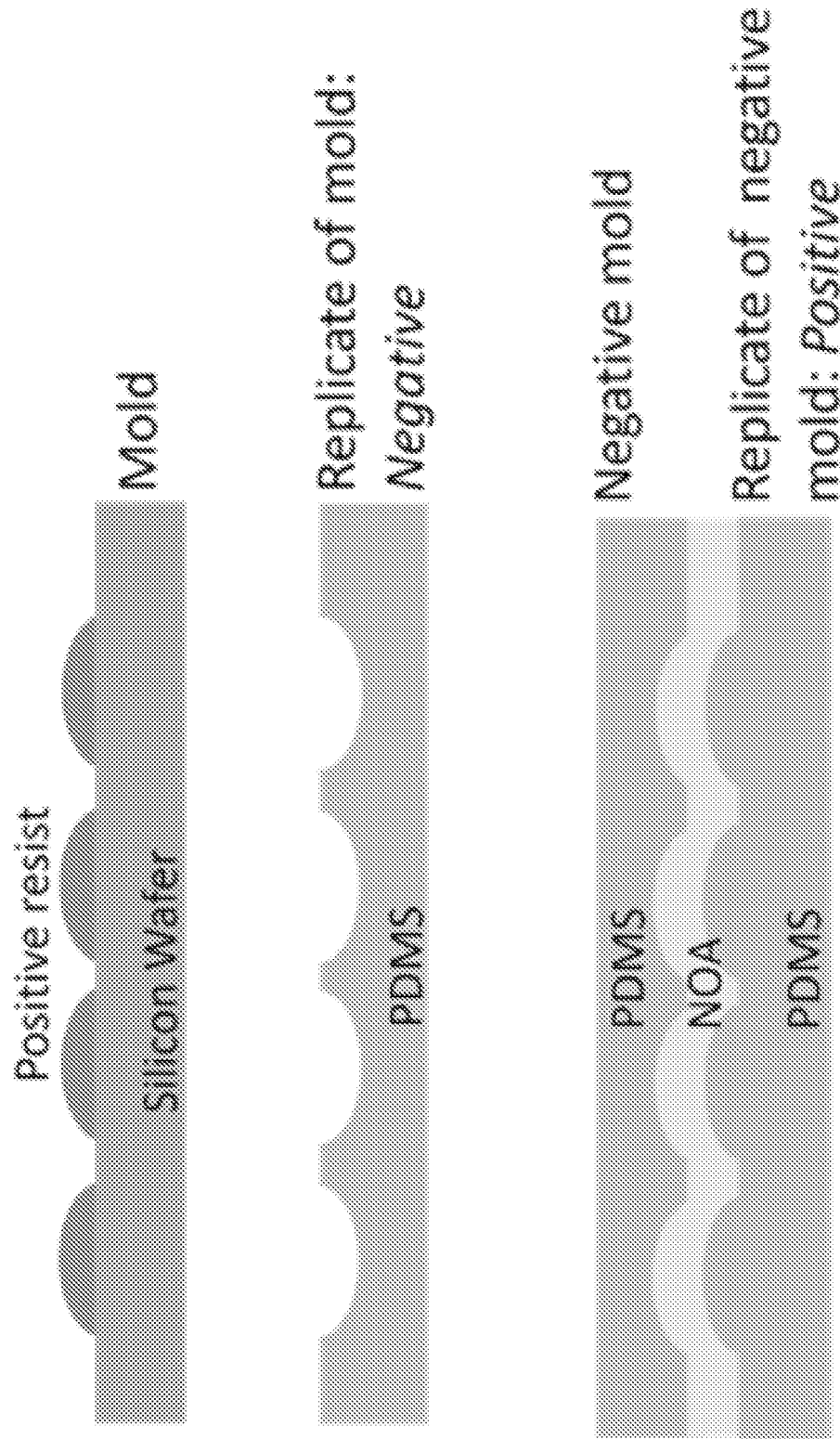
FIG. 15 shows according to an exemplary embodiment of the invention fabrication steps of a ceiling layer of the auxetic microfluidic sensor.

For the auxetic sensor version, the only difference in manufacturing was in the step 4 of FIG. 13, in which we have used a patterned film instead of a flat film as the bottom layer. The patterning was done as shown in FIG. 15.

Variations and Modifications
  a. The microfluidic strain sensing principles could be used for wide range of medical applications where strain sensing is necessary. Biomedical applications other than glaucoma management could be listed as; physiotherapy monitoring (e.g. at joints in hand injuries), speech recognition, fetus/baby monitoring, tremor diseases, robotics etc.
  b. Microfluidic strain sensing can be used for biosensing and biochemical sensing. For example, it can be used to monitor to measure the strain applied by cells on a surface. Mechanical cues play important role in cellular processing such as cell differentiation, apoptosis, and motility. Cells senses and exerts forces on substrate that they grow. Tumor cells generate more forces than regular cells. Shear stress, one of the leading physical cues is causing upregulation of genes activated by mechanic signals. Understanding mechanical cues generated by cells will be crucial to understand cancer progression which is triggered by mutations of mechanotransduction pathways of cells. Our strain sensor will provide direct monitoring of direct cancer cells signaling under exposure of different physical and mechanical cues. Therefore, it will bring novel approach in cancer studies. By using our sensor, new biomarkers will be discovered as well as new drug therapies could be implemented. These devices will also help in several other conditions including regulation of synaptic plasticity of neurons as forces are one of the key factors for progress of synaptic plasticity.

Figure 16:
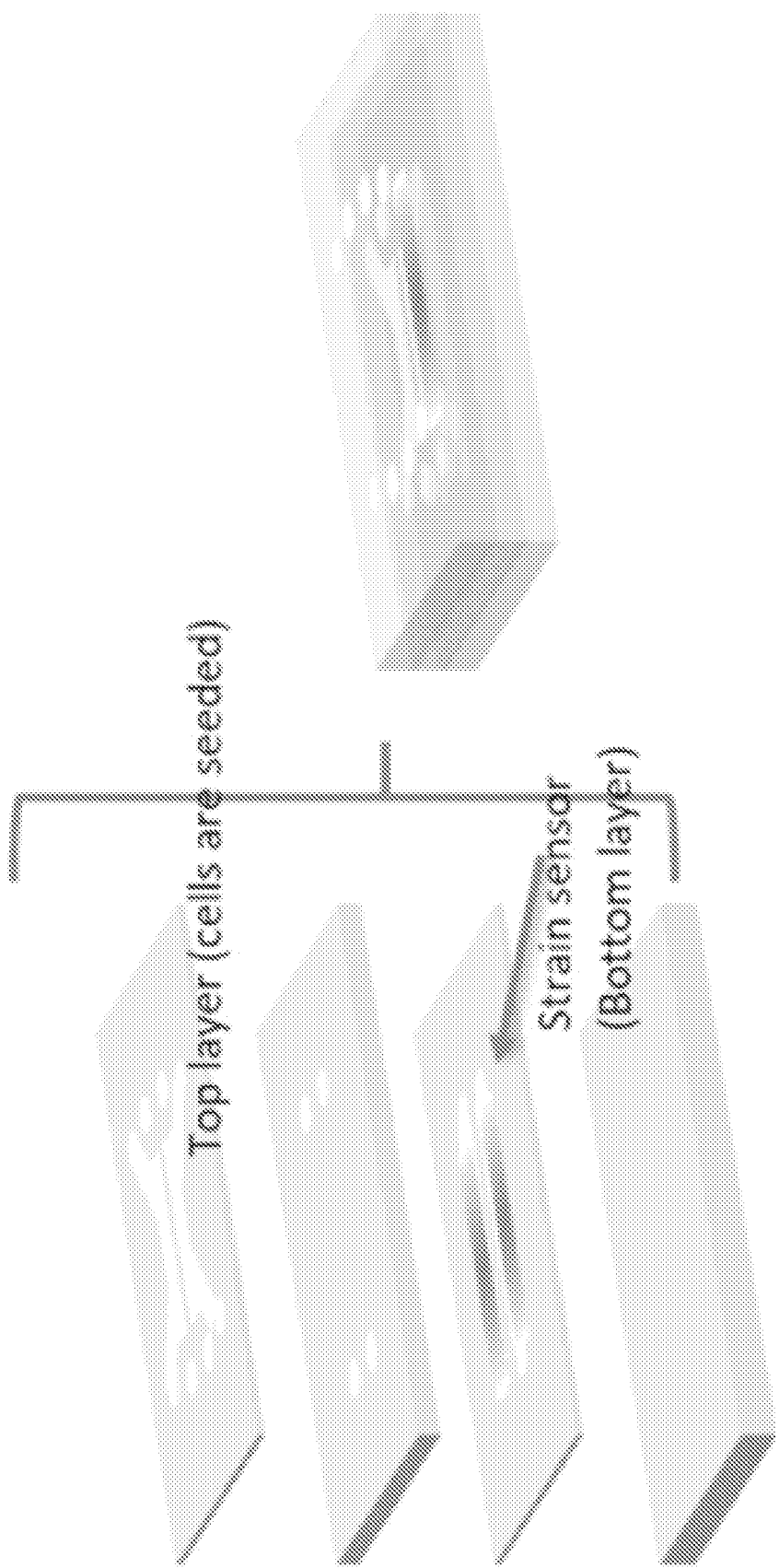
FIG. 16 shows according to an exemplary embodiment of the invention a strain sensor for biomechanics of cancer cells. In the bottom channel, a strain sensor is placed meanwhile cells are seeded in the top channel.

To understand cell's response to different conditions two layers of microfluidic channels can be built as shown in FIG. 16. As cells grow, we could image the strain sensor on the bottom channel. This will provide tissue stiffening. Top channel can also be manipulated by applying different flow rate which changes the shear stress. In this design, cells mechanical response can be observed while they are being mechanically manipulated. This design will be used in biomarker and drug development.

Cancer tissues as they progress shows more stiffer character. In average, cancer cell will have 4 times stiffer than regular tissues. Understanding earlier stiffness of cancer cells will lead to earlier cancer detection. The strain sensor could be incorporated into patches which can be externally used on the skin. Specifically, it could be used in skin and breast cancer types. Such patches with infrared beads embedded in microchannel could be optimized and implanted to internal organs in the case of ovarian cancer, liver and brain cancers. Especially, these patches could be implanted after severe tumor removal surgeries to monitor cancer reoccurrence. Combining microfluidics-based strain sensors with flexible silicon electronics will enable multiplexed measurements on three dimensional soft tissues in vivo. This signal could be transferred to cloud-based system using wi-fi embedded technologies. Overall, the strain sensors incorporated with advance electronics will provide continuous monitoring of tissues which carries high chance of cancer reoccurrence.

Figure 17:
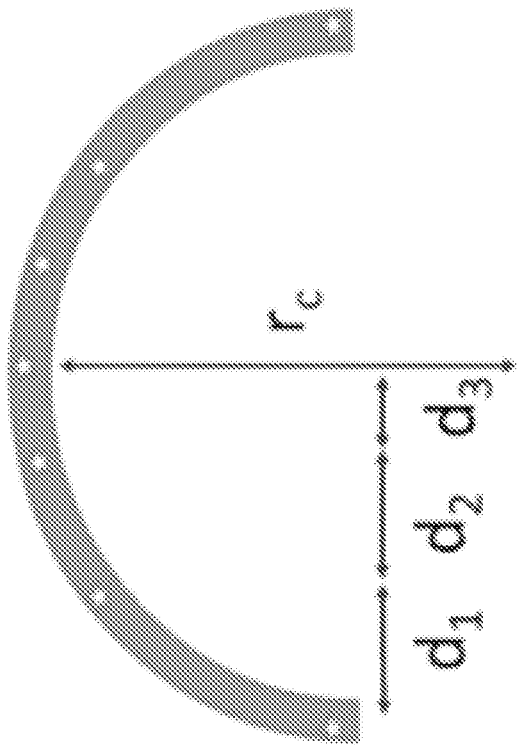
FIG. 17 shows according to an exemplary embodiment of the invention a top view and a side view of a contact lens and the location of the shapes. Besides star shapes in the top view and side view other example shapes can also be provided. The combinations of these shapes can also be used.
Figure 17:
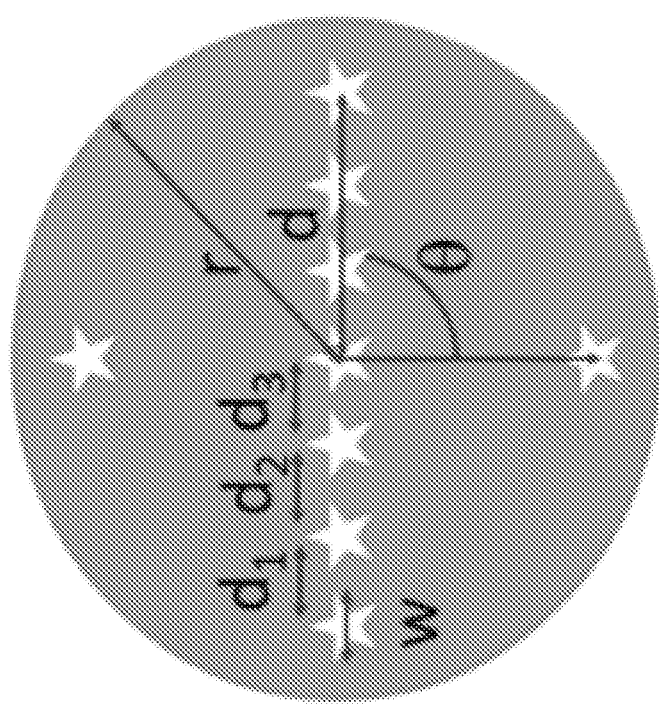
Figure 17:
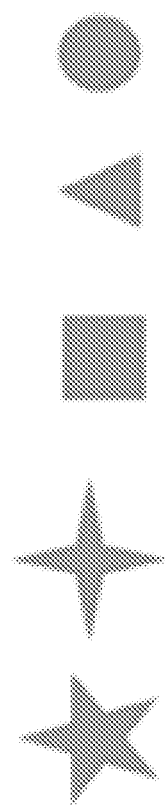
Figure 18:
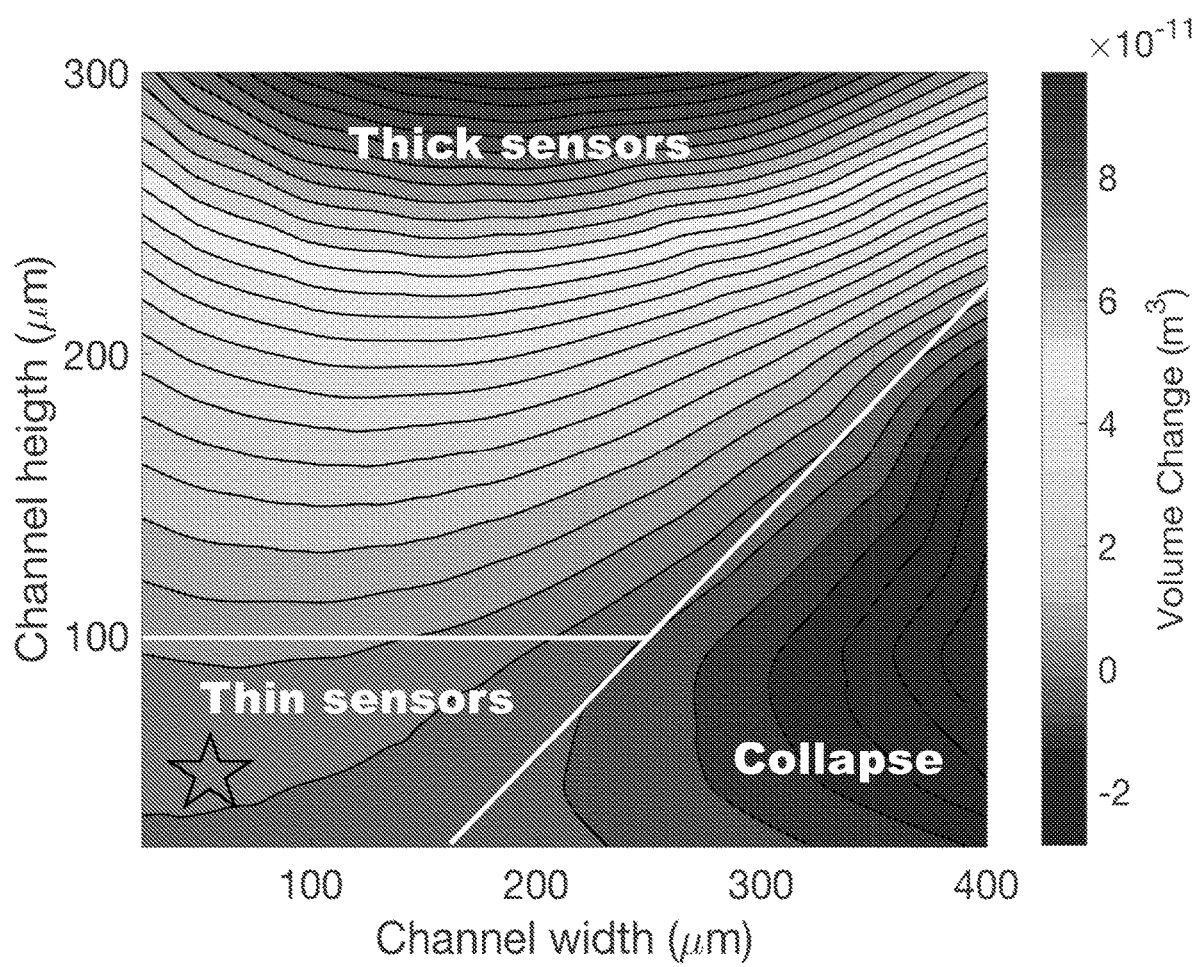
FIG. 18 shows according to an exemplary embodiment of the invention Comsol results where 50 micrometers high and 50 micrometers wide channels provide close to the optimal sensitivity while maintaining thin devices. Star shape in FIG. 18 shows the optimal geometrical parameters for maximum volume change (i.e., sensitivity) while maintaining the device thin.

3) The miLenS can either be manufactured by: i) embedding strain sensor with the desired shape/size in to a contact lens, as described or ii) directly patterning the desired topographies on the surface of the contact lens through soft lithography where features on a mold transferred to the contact lens.
  4) The distance between the microscopic geometric features on the contact lens can be directly measured instead of using microfluidics. This distance will change as a function of IOP. The geometric shapes and patterns of these features should be carefully selected to maximize the sensitivity to IOP. The IOP will be measured based on the imaging of contact lens sensor with geometrical features (geoLenS) similar to miLenS. FIG. 17 shows the top and side views of the example geoLenS. The location and shapes of the microscopic features to be used for IOP determination are shown. Besides the star shape shown in the top view and side view, other example shapes are also provided. The combinations of these shapes can also be used. In the top view, the radius of the contact lens is denoted by r and the value of r can be between 0.5 and 1 cm. 0, shows the angle between the features positioned at the periphery of the contact lens and it determines the number of features that will be placed angularly on a contact lens. 0 could be in between 10° (36 features at the periphery) and 180° (Two features at the periphery). Minimum of two features needed on the contact lens. $d_1, d_2, d_3, \ldots d_n$ denote the distances between consecutive features and can be between 0.01 to 1 cm. The total distance $d=d_1+d_2+d_3+ \ldots +d_n$ should be smaller than r. The radius of curvature of the contact lens, $r_c$, shown in side view can be between 0.5 to 1 cm. The characteristic width of features, w could be 0.001 to 0.5 cm.

As the TOP changes, the distances between peripheral features, e.g., $d_1$, change and can be used as a measure of the TOP change. The distances between central features, e.g., $d_2$ or $d_3$, or the width of any feature, w, can be used as a reference measurement because they do not change in response to IOP. The distance between the opposing features at the periphery (total distance is 2d) changes the most as response to TOP change. The distance of any one of the geoLenS features to the known features of the eye (i.e. iris border) can be detected as a measure of IOP.

To test the feasibility of the concept proposed above, we fabricated a contact lens, which was made of PDMS and has thickness ~250 um. For testing, we fabricated a realistic eye model made of PDMS as shown in U.S. Provisional Patent Application 62/556,366 filed Sep. 9, 2017 (FIG. 19—left therein), which is incorporated herein by reference.

The radius of curvature of the eye model changes ~4 µm/mmHg (3 µm/mbar) and this is very close to the behavior of human's eye.

We put marks on the contact lens and we placed it on the eye model we created as shown in U.S. Provisional Patent Application 62/556,366 filed Sep. 9, 2017 (FIG. 19—right therein), which is incorporated herein by reference. These marks served as probes and enabled us to measure the change in distance between different locations on the contact lens as a function of applied pressure. We had four levels of applied pressure in the eye model varying from 25 mbar to 100 mbar. We sampled four locations on the contact lens (3 distance measurements) and distances between these locations are plotted as a function of applied pressure as shown in U.S. Provisional Patent Application 62/556,366 filed Sep. 9, 2017 (FIG. 29 therein), which is incorporated herein by reference. The point located on the center of the contact lens is labeled as location '1' and the number is increased as the points located further from the center (e.g., location '2'). The distances between different marked points (e.g., location '1' to location '2') were measured. In FIG. 20, blue, red, and green lines show the distance as a function of applied pressure for location 1 to 2, location 2 to 4, and location 4 to 6, respectively. Corresponding linear fits are plotted as well. Overall, the preliminary results show that the distances between different locations on the geoLenS follow a linear function of applied pressure and this is in a measurable range.

5) The geoLenS features can be fabricated similar to miLenS or they can just be marked with an ink.

6) The miLenS reservoir channels can have a serpentine shape instead of circular.
7) The device can be used as a temperature sensor as it is sensitive to thermal expansion of the material.
8) The device is insensitive to air pressure changes. It can be used in vacuum, e.g. in space applications.
9) The images can be taken by a smartphone camera, a special handheld camera, or by a wearable camera. The images can be taken directly across the eye, at 45° angle or at 90° angle or any angle between 0°-90° angle.
10) The front or back camera of the smartphone can be used for imaging.
11) The images can be collected by the patient, at will or automatically when the patient is reading something on the phone.
12) The image analysis can be made by the microprocessor of the camera or can be transferred to a main server for further processing.
13) The patient can pay for subscription to cloud services such as data storage, analysis etc.
14) The miLenS channels can be filled with a colored liquid to improve the contrast on the iris or sclera.

ADDITIONAL TECHNICAL NOTES

The invention pertains to a closed microfluidic network for strain sensing applications. The device has strain sensitivity of 2-15 mm interface movement per 1% strain depending on the number of rings. The sensitivity can be increased even further by increasing the number of rings. It is robust enough to withstand pressure changes that are applied for 24 hours and has a lifetime of months. These features make it attractive for applications where extremely strain levels smaller than 0.1% need to be measured for time periods longer than 2 hours. We have embedded the sensor into a contact lens for monitoring intraocular pressure (IOP). The required detection limit for TOP is 1 mmHg. This corresponds to a strain of 0.05%. We have achieved this strain detection limit by designing a liquid reservoir network which includes multiple microfluidic channels as a liquid reservoir. The liquid reservoir network is connected to a sensing channel and the sensing channel is connected to an air reservoir. These three components form a closed system. The sensor with its three components in one possible configuration is shown in FIG. 3. FIG. 3 is the top view of the sensor showing when it is embedded in a contact lens. The sensor is filled from the inlet with a working liquid, using only capillary forces. When the working liquid reaches the outlet, both inlet and outlet are sealed using the sensor material to form a closed system with a fixed liquid volume inside. At this point the liquid fills the sensing channel, approximately half of its total length, creating a liquid/air interface. Both the contact lens and the sensor are made of elastomers such as silicone and polyurethane but can be made of other materials such as silicone/hydrogel.

The sensor works based on volume amplification of microfluidic liquid reservoir network when it is stretched under tangential forces. The working principle of the sensor is described in FIG. 4. Here, another configuration of the sensor components, where they are linearly distributed instead of radially distributed, is used for simplicity. The side view of the sensor with a liquid reservoir which could have multiple chambers, A), versus a single wide chamber, B), is compared. When the sensor is stretched under tangential forces, the shape of the sensor and of its components change as depicted in A*) and B*), respectively. 410-A and 410-B are representations of the possible stress regions on the sensor in the vicinity of liquid reservoir. For reference, the total initial length of the sensor is shown as 1-1', total initial liquid reservoir network width is shown as 2-2', and initial position of the liquid air interface is shown as 3. There are three notable mechanical changes which could occur when such a closed microfluidic network is stretched under tangential force;

i. Elongation: When A*) and B*) are compared with A) and B), respectively, it can be seen that the total sensor length, (1-1'), will increase due to elongation. Similarly, the liquid reservoir network width, (2-2'), will also increase.
 ii. Collapses: In the case of single reservoir, the thin membrane above the liquid reservoir will collapse due to the induced stress and due to the low rigidity of this membrane, as shown in B*). When multiple chambers with higher rigidity membranes are used, the collapses will not occur, or will decrease significantly, as shown in A*).
 iii. Liquid reservoir volume increase and resulting vacuum effect: When the liquid reservoir width is elongated, its total volume will increase if the membrane collapses can be prevented or reduced significantly. This volume increase can be amplified if the liquid reservoir consists of multiple chambers with small widths as shown in B*). The amplification will be even higher when auxetic patterns are created on the membrane of the small reservoir chambers. When the volume of the liquid reservoir increases, this causes a vacuum effect and this vacuum pulls the liquid/air interface position (3) towards the liquid reservoir. The movement of this interface, in μm, per TOP change, in mmHg, is defined as sensitivity. Each 1 mmHg TOP change causes a strain of 0.05% according to literature. This strain causes approximately 100 μm position change on the interface position.

Another factor that should be considered for maximum sensitivity is the Young's modulus (E) of the sensor material. Increasing the E reduces the comfort. When contact lenses with high lubricity is used for improved comfort, the contact friction between the cornea and sensor/lens will decrease, which will cause slipping and decreased sensitivity, especially for high E sensors. According to our experimental and simulation results, the optimal E is in the range of 0.2-10 MPa for maximum sensitivity and comfort. As the E is reduced below 2 MPa, the width of the reservoir channels also has to be reduced below 100 μm.

What is claimed is:

1. A method for monitoring an intraocular pressure change of an eye, the method comprising:
 providing a contact lens having integrated therein a first microfluidic strain sensor having a volume sensitive to an applied strain, the first microfluidic strain sensor comprising:
   a first fluid reservoir containing a first fluid;
   a second fluid reservoir containing a second fluid which volume changes when the strain is applied; and
   a sensing channel connecting the first fluid reservoir and the second fluid reservoir;
 wherein a first fluid—second fluid equilibrium pressure interface and equilibrium are established within the sensing channel, and wherein the first fluid—second fluid equilibrium pressure interface and equilibrium fluidically change as a response to one or more of (i) radius of curvature variations on a cornea or (ii) to mechanical stretching and release of the cornea; and measuring the intraocular pressure of the eye by observing the first fluid—second fluid equilibrium pressure interface and equilibrium.

2. The method of claim 1, wherein at least one ring is formed within the contact lens for the second fluid reservoir, wherein the first fluid reservoir is positioned inside the at least one ring.

3. The method of claim 1, wherein the second fluid reservoir volume is sensitive to a tangential force on the eye relative to a radial force on the eye wearing the contact lens.

4. The method of claim 1, wherein the second fluid reservoir has a stiffness in a radial direction and/or a smaller channel width relative to a stiffness in a tangential direction.

5. The method of claim 1, wherein the contact lens is a silicone contact lens, a hydrogel contact lens or a combination thereof.

6. The method of claim 1, wherein the sensing channel has a strain sensitivity of about 4.5 mm interface movement per about 1 percent strain applied to the second fluid reservoir.

7. The method of claim 1, wherein the sensing channel has an inner diameter of about 1-10 mm.

8. The method of claim 1, wherein the sensing channel has an inner diameter of about 5-12 mm with a cross sectional area of $10^{-11}$-$10^{-8}$ m$^2$.

9. The method of claim 1, wherein the second fluid reservoir has one or more chambers.

10. The method of claim 1, wherein the second fluid reservoir has one or more chambers with concentric rings.

11. The method of claim 1, wherein the second fluid reservoir has one or more chambers with concentric rings, wherein the concentric rings are connected at one or more locations.

12. The method of claim 1, wherein the second fluid reservoir has one or more chambers with concentric rings, wherein each concentric ring is a different width.

13. The method of claim 1, wherein the second fluid reservoir has a surface with a pattern.

14. The method of claim 1, wherein the second fluid reservoir has a ceiling and a floor, the ceiling having a convex shape and wherein the ceiling is curved towards the floor.

15. The method of claim 1, wherein the contact lens has no actively controlled components or electrical components.

16. The method of claim 1, wherein the microfluidic network is transparent.

17. The method of claim 1, wherein the microfluidic network is oleophobic.

18. The method of claim 1, wherein at least a portion of the first microfluidic strain sensor is arranged along a peripheral area of the contact lens.

19. The method of claim 1, wherein the first microfluidic strain sensor is arranged as a ring.

20. The method of claim 1, wherein the first microfluidic strain sensor has a position that does not interfere with a vision pathway of a user through the contact lens.

21. The method of claim 1, wherein a second microfluidic strain sensor is integrated into the contact lens, the second microfluidic strain sensor comprising a third fluid reservoir, a fourth fluid reservoir, and a second sensing channel; wherein the second sensing channel contains a third fluid—fourth fluid interface between the third fluid reservoir and the fourth fluid reservoir, the third fluid—fourth fluid interface moving within the second sensing channel in response to axial strain exerted on the contact lens.

22. The method of claim 21, wherein at least a portion of the second microfluidic strain sensor is arranged along a peripheral area of the contact lens.

23. The method of claim 21, wherein the first and second microfluidic strain sensors are independent of each other.

24. The method of claim 21, wherein the second microfluidic strain sensor is closed.

25. The method of claim 21, wherein the third fluid reservoir contains a third fluid comprising a liquid.

26. The method of claim 21, wherein the fourth fluid reservoir contains a fourth fluid comprising a gas.

27. The method of claim 21, wherein the third fluid—fourth fluid interface is a liquid-gas equilibrium pressure interface.

28. The method of claim 21, wherein the first or second microfluidic strain sensor is at least partially made of an auxetic metamaterial.

29. The method of claim 21, wherein the first or second microfluidic strain sensor is at least partially made of polyurethane.

30. The method of claim 21, wherein the first or second microfluidic strain sensor has a shape which is at least partially circular, linear, or both.

31. The method of claim 1, wherein the first microfluidic strain sensor is closed.

32. The method of claim 1, wherein the first fluid comprises a gas.

33. The method of claim 1, wherein the second fluid comprises a liquid.

34. The method of claim 1, wherein the first fluid—second fluid equilibrium pressure interface is a liquid-gas equilibrium pressure interface.

35. The method of claim 21, wherein the first or second microfluidic strain sensor is at least partially made of a strain responsive material.

* * * * *